United States Patent [19]
Atkins et al.

[11] Patent Number: 5,932,435
[45] Date of Patent: Aug. 3, 1999

[54] SCREENING ANTISENSE AND RIBOZYME NUCLEIC ACIDS IN *SCHIZOSACCHAROMYCES POMBE*

[75] Inventors: David Atkins, Darlinghurst; Gregory Martin Arndt, Malabar; Jonathan Goulder Izant, Northbridge, all of Australia

[73] Assignee: Gene Shears Pty. Ltd., New South Wales, Australia

[21] Appl. No.: 08/727,449

[22] PCT Filed: Apr. 20, 1995

[86] PCT No.: PCT/AU95/00235

§ 371 Date: Oct. 18, 1996

§ 102(e) Date: Oct. 18, 1996

[87] PCT Pub. No.: WO95/29254

PCT Pub. Date: Nov. 2, 1995

[30] Foreign Application Priority Data

Apr. 20, 1994 [AU] Australia .................. PM 5169/94

[51] Int. Cl.⁶ .................. C12Q 1/02; C12Q 1/68; C07H 21/04
[52] U.S. Cl. .................. 435/29; 435/4; 435/6; 435/172.3; 536/24.5
[58] Field of Search .................. 435/4, 6, 29, 172.3, 435/254.2; 536/24.5

[56] References Cited

U.S. PATENT DOCUMENTS 5,443,962  8/1995  Draetta et al. .................. 435/29

OTHER PUBLICATIONS

Forsburg, "Comparison of *Schizosaccharomyces pombe* expression systems", Nucleic Acids Res. 21(12): 2955–2956, Jun. 1993.

Fleig et al., "A dominant negative allele of p34–cdc2 shows altered phosphoamino acid content and sequesters p56–cdc13 cyclin", Mol. Cell. Biol. 12(3): 2295–2301, May 1992.

Schweingruber et al., "Regulation of pho1–encoded acid phophatase of *Schizzosaccharomyces pombe* by adenine and phosphate", Curr. Genet. 22: 289–292, Oct. 1992.

Atkins et al., "Artificial ribozyme and antisense gene expression in *Saccharomyces cerevisiae*", Antisense Res. Devel. 4: 109–117, 1994.

*Primary Examiner*—Jasemine C. Chambers
*Assistant Examiner*—Scott D. Priebe
*Attorney, Agent, or Firm*—John P. White; Cooper & Dunham LLP

[57] ABSTRACT

The present invention relates generally to an in vivo system for gene expression and, more particularly, to the use of the system to screen for molecules which are capable of inhibiting, reducing, altering or otherwise modulating expression of a target nucleotide sequence or the activity of a gene product. The in vivo system of the present invention is particularly but not exclusively useful for screening for antisense, sense or ribozyme constructs or transdominant polypeptides, small peptides or other chemical compounds that are capable of inhibiting, reducing, altering or otherwise modulating expression of target genes or target genetic sequences or the activity of target gene products of commercial importance such as in medical, agricultural and industrial fields.

13 Claims, 23 Drawing Sheets

Thiamine:    +    −    +    −    +    −
(4 μM)

FIG. 3
Antisense Genes
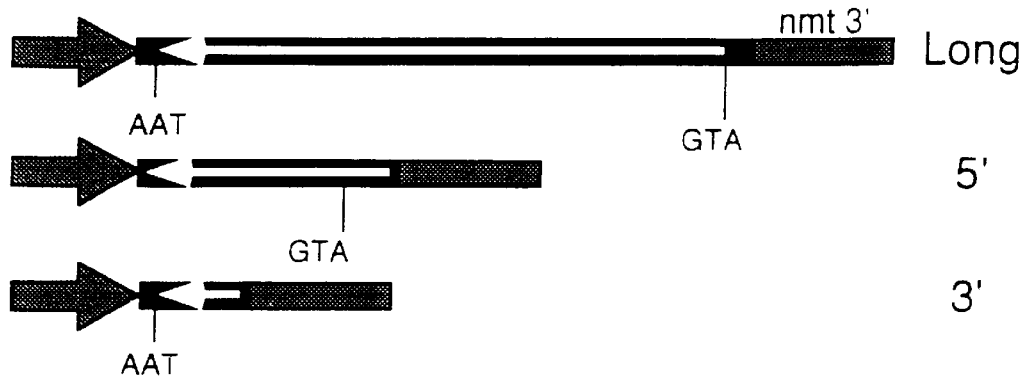
Control (sense-orientation) Genes
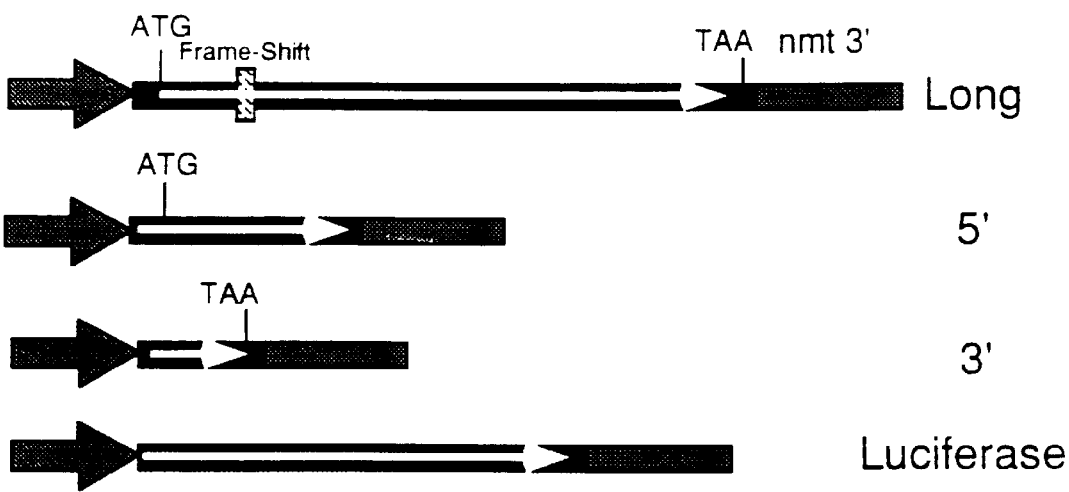

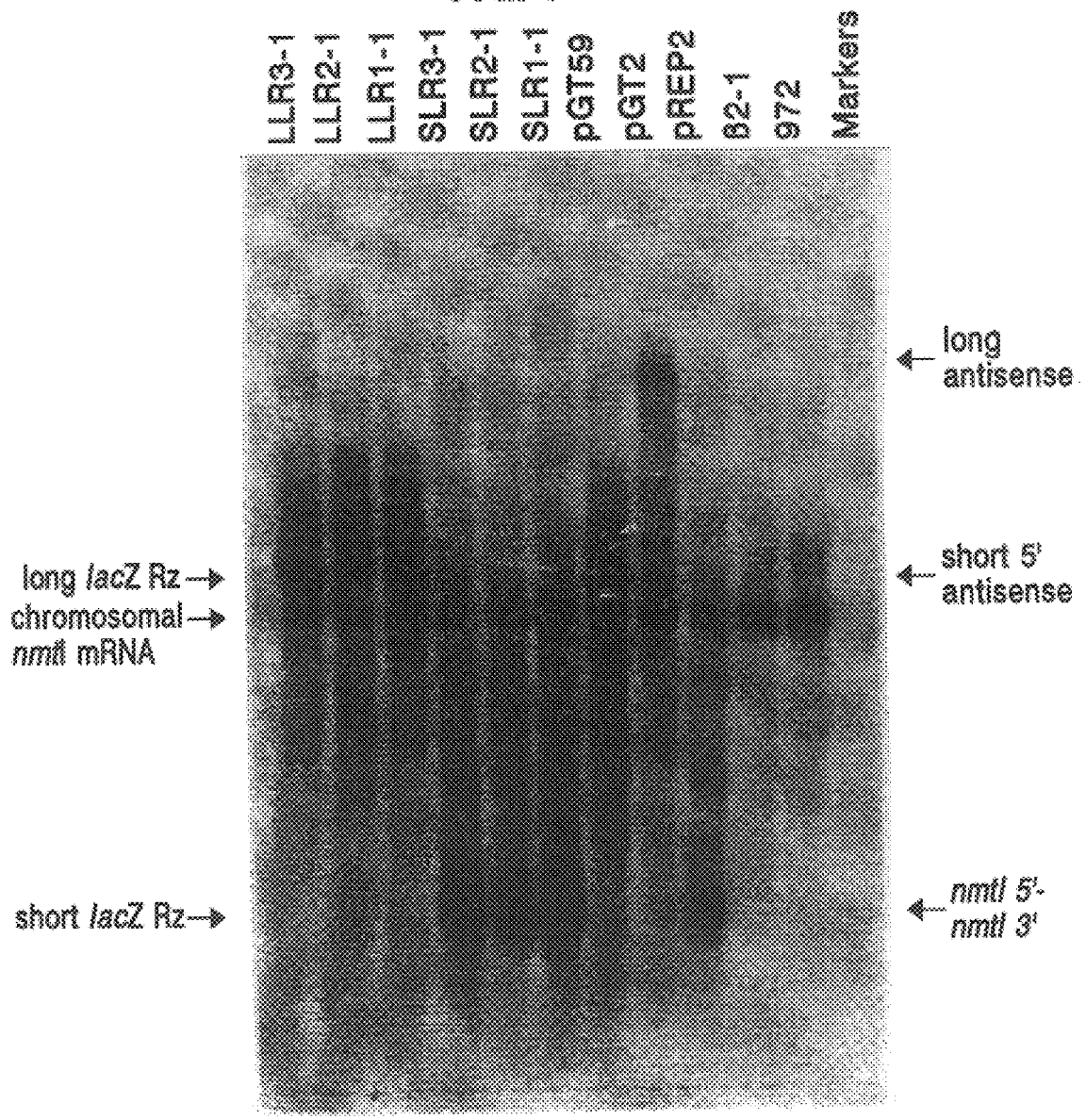

Target Gene (Chromosome III)

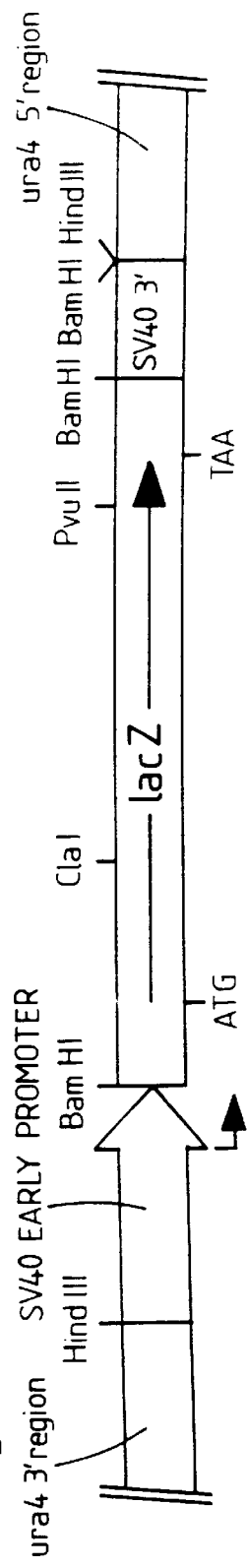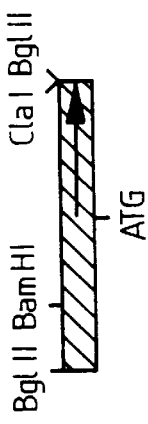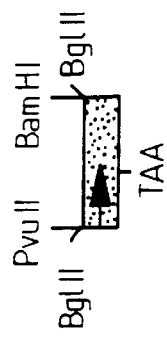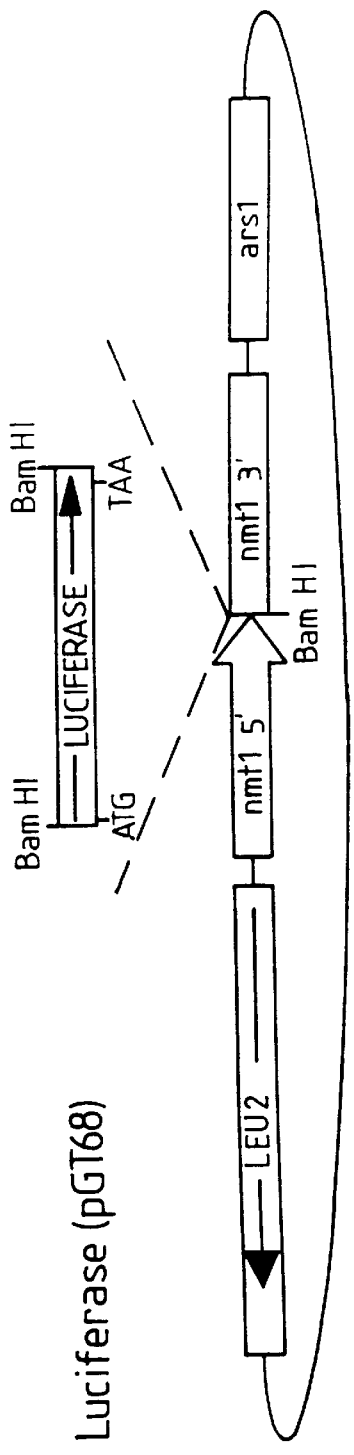
FIG. 12B

५,९३२,४३५

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

AAGAGATCTG CCTCTGAGCT ATTCCAGAAG TAGTG                    35

(2) INFORMATION FOR SEQ ID NO:2:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

AAGAGATCTC ATCGATAATT TCACCGCCGA AAGGC                    35

(2) INFORMATION FOR SEQ ID NO:3:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

AAGAGATCTT CAGTATCGGC GGAATTACAG CTGAG                    35

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

AAGAGATCTC AATGTATCTT ATCATGTCTG GATCC        35

SCREENING ANTISENSE AND RIBOZYME NUCLEIC ACIDS IN *SCHIZOSACCHAROMYCES POMBE*

This application is a national stage application filed under 35 USC 371 of PCT/AU95/00235, filed Apr. 20, 1995.

The present invention relates generally to an in vivo system for gene expression and, more particularly, to the use of the system to screen for molecules which are capable of inhibiting, reducing, altering or otherwise modulating the expression of a target nucleotide sequence or the activity of a gene product. The in vivo system of the present invention is particularly but not exclusively useful for screening for antisense, sense or ribozyme constructs or transdominant polypeptides, small peptides or other chemical compounds and which are capable of inhibiting, reducing, altering or otherwise modulating expression of target genes or target genetic sequences or the activity of target gene products of commercial importance such as in the medical, agricultural and industrial fields.

Sequence Identity Numbers (SEQ ID NOs.) for the nucleotide sequences referred to in the specification are defined just prior to the claims.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The rapidly increasing sophistication of recombinant DNA technology is greatly facilitating the efficacy of many commercially important industries including areas of medicine, agriculture, horticulture and fermentation. An important tool in recombinant DNA technology is the use of antisense molecules, sense molecules, ribozymes and other genetic sequences and/or non-nucleotide molecules such as peptides or chemical agents to affect expression of genetic sequences.

Ribozymes are RNA molecules which possess highly specific endoribonuclease activity. In particular, they comprise a hybridising region which is complementary in nucleotide sequence to at least part of a target RNA and a catalytic region which is adapted to cleave the target RNA. An example where ribozymes are well described is Haseloff J. and Gerlach W *Nature* 334: 586–591, 1988 and in International Patent Application No. WO 89/05852. Antisense molecules are genetic constructs which are generally complementary in nucleotide sequences to target mRNA. Although the exact mode of action of antisense molecules is unclear, it is possible that they form a duplex with all or part of target mRNA with a consequential interferring effect on the mRNA transcript. Sense nucleotide constructs are used in co-suppression and have been shown to be effective in reducing expression of, for example, plant genes.

There is a need to develop effective approaches for rapidly evaluating molecules such as antisense, sense and ribozyme constructs, transdominant polypeptides, small peptides and other chemical compounds as potential effector molecules in modulating expression of target genetic sequences or the activity of products encoded thereby.

Microorganisms have previously been considered as a convenient in vivo model system for testing for compounds which affect, for example, their viability or ability to grow. Microorganisms are advantageous experimental hosts for molecular and genetic analysis. Their assets include a short generation time, readily available techniques for growing and analysing large numbers of cells and the relative ease of introducing and recovering nucleic acids from these cells. More than $10^{11}$ microorganisms can readily be grown on inexpensive nutrients whereas the production of even $10^8$ mammalian cells is slow and expensive. However, while bacterial cells have been used in the elucidation of many basic aspects of gene expression, they lack many of the fundamental features of eukaryotic RNA physiology. Bacterial cells have no nuclear compartment, contain a reduced number of completely distinct RNA and DNA binding proteins, have few or no spliced mRNAs, no spliceosomal machinery for intron removal, and use a different system for the initiation of protein translation.

Yeast cells, on the other hand, have greater benefits as experimental models because they have all the basic features of higher eukaryotes such as plant and animal cells plus a generation time reminiscent of bacteria. There is a large set of molecular and genetic techniques available for introducing, analyzing and recovering nucleic acids in these cells making them amenable to genetic as well as biochemical investigations. It is possible to generate populations of yeast cells that are large and complex enough to facilitate thorough genetic analysis.

However, many laboratories have attempted unsuccessfully to use antisense and ribozyme technology in the budding yeast *Saccharomyces cerevisiae*. This yeast has been studied more thoroughly than any other eukaryotic microorganism and a large range of genetic and molecular tools are currently available. To date, there have been no reports of the completely successful use of antisense and/or ribozyme constructs to suppress gene expression in *S. cerevisiae* even using target systems which have worked well in animal and plant cells. It is surprising that *S. cerevisiae* is apparently so recalcitrant to, for example, antisense and ribozyme inhibition. Artificial antisense approaches have been successfully explored in virtually every other eukaryotic system available for molecular genetic studies such as in mammalian cells, Drosophila, plants and the slime mould *Dictyostelium discoidium*.

The fission yeast *Schizosaccharomyces pombe* also has a highly characterised genetic system. There are a number of features of *S. pombe* that render these cells more similar to human and other higher eukaryotic cells than *S. cerevisae* including chromatin structure and behaviour, intron distribution and small nuclear ribonucleoprotein particle RNAs and proteins. Furthermore, *S. pombe* cell division cycles are very similar to those of higher eukaryotic organisms. This makes *S. pombe* a potentially valuable model for studying higher eukaryotic gene expression including expression of animal and mammalian (e.g. human) genes, insect genes and plant genes.

In work leading up to the present invention, the inventors sought to evaluate *S. pombe* as a potential model for studying altered expression of target genes. The inventors discovered that certain genetic constructs are expressed in *S. pombe* and lead to altered modulation of expression including suppression of target genes. The present invention, therefore, provides for the first time, a suitable microbial model of gene expression for the efficient screening of genetic constructs such as antisense, sense and ribozyme constructs and molecules such as transdominant polypeptides, small peptides and other chemical compounds as potentially effective agents capable of modulating expression of target genes of eukaryotic, prokaryotic or viral origin or capable of modulating activity of products of such genes. The present invention is useful, for example, in screening bacteriophage display libraries for novel protein, polypeptide or peptide encoding sequences for effectors of gene expression. The present invention is particularly useful in the screening of potential diagnostic and therapeutic molecules for the medical and animal health industries as well as a range of agrochemical molecules for the plant and crop industries.

Accordingly, one aspect of the present invention contemplates a method of identifying molecules capable of inhibiting, reducing or otherwise modulating expression of a target gene or activity of a target gene product, said method comprising generating a strain of *Schizosaccharomyces pombe* capable of expressing said target gene, introducing to said strain of *S. pombe* an effective amount of said molecule to be tested and determining the effect of said molecule on expression of said target gene or activity of the product of the target gene.

The molecules are preferably genetic constructs such as antisense, sense nucleotide sequences or ribozymes relative to a target gene, or other nucleotide sequences such as oligonucleotides, random nucleotide sequences or nucleotide sequences selected for cleavage in vitro. The present invention extends, however, to non-nucleotide molecules such as transdominant polypeptides, small peptides and chemical compounds as well as to synthetic nucleotide molecules or nucleotide analogue molecules. The term "modulating expression" and other like expressions includes up-regulating and down-regulating activity of a product of a target sequence. Accordingly, molecules which so modulate expression or activity may be agonists or antagonists. Furthermore, the present invention extends to identifying agents, such as for example, ribozymes, antisense and sense nucleotide molecules who activity is regulated by cellular factors including switching mechanisms and intracellular address signals. Addtionally, in some circumstances, the level of effect on expression may be enhanced by increasing the level of modulating molecules such as antisense, sense or ribozyme molecules.

The method of the present invention may also be used in conjunction or in combination with or as an adjunct to in vitro evaluation experiments to identify target molecules of interest. Accordingly, the method of the present invention may be used in random as well as rational drug design. This would be particularly useful, for example, for the further evaluation of a ribozyme which is effective in vitro. In one embodiment, further nucleotide sequences are added to the ribozyme to facilitate, for example, targetting the ribozyme to a particular sequence, penetration of the cell or to otherwise facilitate is activity.

The term "gene" is used in its most broadest sense to include a classical genomic gene as well as a genetic sequence comprising only the coding portions of a gene (i.e. exons) and a cDNA sequence corresponding to a mRNA transcript. A "gene" as contemplated herein especially in relation to a target gene includes a naturally occurring gene, a partial gene, a synthetic gene and a fusion between a target gene and another gene or genetic sequence. A "gene", therefore, is considered herein to include any target nucleotide sequence and may be of eukaryotic, prokaryotic or viral origin. Preferably, the target gene is "exogenous" or "non-indigenous" to *S. pombe* meaning it is a heterologous gene which has been introduced by transformation, conjugation, electroporation or other means to the yeast cell. However, the target gene may alternatively be "endogenous". Particularly preferred endogenous or homologous (also referred to herein as "indigenous") *S. pombe* genes are those which encode cell cycle proteins, modulate cell cycles and/or are involved in programmed cell deaths. Such genes and in particular antagonists thereof identified in accordance with the present invention may be useful in the treatment of cancers in mammals such as humans. Other important endogenous genes are *S. pombe* homologues of mammalian (e.g. human) genes. A particularly useful yeast in accordance with this aspect of the present invention has *S. pombe* genes replaced by a mammalian (e.g. human) homologues or comprise homologous animal, mammalian or plant genes or have homologous functions to animal, mammalian or plant genes. An example of such a yeast is a yeast carrying a mutation which is functionally complemented or otherwise substituted by homologous of animal, mammalian or plant genes.

In a particularly preferred aspect of the present invention, the target gene construct comprises either a target sequence or a portion thereof fused to or otherwise operably linked to a nucleotide sequence encoding a reporter molecule. Alternatively, a reporter gene may be inserted in an operable location adjacent to an *S. pombe* gene such as a *S. pombe* homologue of a heterologous (e.g. mammalian) gene. Such a genetic construct when expressed in *S. pombe* may in one form direct the synthesis of a fusion polypeptide having a target gene encoded portion and a reporter molecule portion. In accordance with this aspect of the present invention, a molecule such as a genetic sequence is tested for its ability to alter the expression of the target gene by reference to expression of the reporter gene sequence or activity of the reporter molecule.

In accordance with this aspect of the present invention, there is provided a method of identifying genetic sequences capable of inhibiting, reducing or otherwise regulating expression of a target gene, said method comprising generating a strain of *S. pombe* capable of expressing said target gene in a genetic construct which further comprises a reporter gene capable of providing an identifyable signal, introducing to said strain of *S. pombe* an effective amount of a genetic construct to be tested and assaying for an inhibition, reduction, or down-regulation of expression of said reporter gene. In some assays up-regulation may also be tested. In an alternative embodiment, chemical agents including transdominant polypeptides, small peptides or other chemical compounds are tested for their modulatory ability.

The rationale behind this method is the production in the yeast cell of a single mRNA transcript encoding both the target gene product or a portion thereof and reporter molecule. Generally, the reporter molecule will be encoded by a nucleotide sequence placed downstream of the nucleotide sequence encoding the target gene product. A genetic sequence is then tested by reference to a change in the detectable reporter molecule.

In a preferred embodiment, the genetic sequence to be tested is an antisense molecule comprising five or more nucleotides, a ribozyme, a triplex, an RNA or protein decoy, a sense molecule for use in sense or co-suppression, transdominant mutant nucleotides, defective interfering RNAs or DNAs or proteins and the like such as naturally occuring or synthetic chemical compounds. In a most preferred embodiment, the genetic sequence to be tested is an antisense molecule, a sense molecule or a ribozyme.

The reporter molecule may be any molecule capable of giving an identifiable signal and may be an enzyme (e.g. β-galactosidase and horse radish peroxidase), confer antibiotic resistance, confer non-antibiotic compound resistance, be a fluorogenic compound, a fluorescent protein, a chemiluminescent compound, a biotynolated compound, an essential growth factor, cell cycle protein or a molecule capable of giving a cell a defined phenotype such as size, colour and cell surface phenotype (e.g. rough or smooth edges, concave or convex colonies). The β-galactosidase gene is a particularly useful reporter molecule. The reporter molecule may also be a fusion reporter molecule between the above reporter molecules or between S. pombe homologous and heterologous genes. Particularly, useful reporter molecules include chloramphenicol acetyl transferase (CAT) [Jones et al Cell 53: 659–667, 1988], β-glucuronidase (GUS [Pobjecky et al Mol. Gen. Genet. 2220: 314–316, 1990], firefly luciferase (LUX), phleomycin resistance gene (ble) [Prentice and Kingston Nucl. Acids. Res. 20: 3383–3390, 1992], green fluorescent protein (GFP) [Chalfie et al Science 263: 802–805, 1994], neomycin phosphotransferase (Neo) which confers resistance to G418 (Gmunder and Kohli Mol. Gen. Genet. 220: 95–101, 1989) and the S. pombe ura4 gene and fusion derivatives thereof (for example see Myers et al Current Genetics 27: 243–248, 1995). Another suitable reporter molecule is adenosine phosphoribosyl transferase (APRT).

The target gene including a fusion target gene construct may be integrated into the chromosome of S. pombe under the control of an endogenous promoter or exogenous promoter or may exist as an extrachromosomal, replicating element. Any number of exogenous promoters may be used such as the SV40 promoter. A suitable endogenous promoter is the regulated S. pombe adh1 promoter.

The genetic sequences to be tested (e.g. an antisense or sense molecule or ribozyme construct) may be introduced to the yeast cell by any number of means including transformation, conjugation, electroporation, amongst others. The genetic sequence may be expressed under an endogenous or exogenous promoter or may be introduced without a promoter.

The present invention permits the rapid screening of genetic sequences having an effect on expression of target genes. The target genes include eukaryotic, prokaryotic and viral genes. Examples of eukaryotic genes include mammalian growth factors and cytokines and their receptors and cancer specified genes and plant genes. Examples of prokaryotic genes include β-galactosidase and pathogen-specific genes. Examples of viral genes include HIV and Hepatitis genes. The subject invention is particularly applicable for the development of a disease model system suitable for screening for useful genetic sequences to target viral, cancer and aberrant "self" genes. The method of the present invention may also be useful as drug screening reagents. For example, receptor genes are engineered and expressed in a reporter gene-dependent manner. The modified yeast is then used in high through-put assays for agonists or antagonists of the receptors.

Although the present invention is exemplified using S. pombe as the in vivo model and β-galactosidase gene as both the target and reporter molecule, the present invention clearly extends to and encompasses other suitable eukaryotic organisms and other reporter molecules.

Other aspects of the present invention include an in vivo model system for screening of molecules capable of inhibiting, reducing or otherwise modulating expression of a target gene or activity of a target gene product, said in vivo model system comprising a strain of S. pombe capable of expressing said target gene wherein molecules to be tested are introduced into said S. pombe and screened for inhibition, reduction or down regulation of said target gene.

The present invention is further described by the following non-limiting figures and examples.

In the figures:

FIGS. 1(A)–1(C) are a representation showing genotypic analysis of S. pombe β-galactosidase strains. The β2-1* ura 4/β-galactosidase locus was used to construct KC4-6.

FIGS. 2(A) and 2(B) are a representation showing regulated gene expression in S. pombe.

FIG. 3 is a diagrammatic representation showing β-galactosidase antisense and control sense orientation genes.

FIGS. 4(A) and 4(B) are a diagrammatic representation showing that antisense RNA inhibits gene expression in S. pombe.

FIGS. 5(A)–5(D) are a diagrammatic representation showing that β-galactosidase gene suppression is transcription-dependent.

FIGS. 6(A)–6(C) are a diagrammatic representation showing long and short-armed lacZ ribozymes containing a single hammerhead cleavage domain.

FIGS. 7(A)–7(C) are a representation showing in vitro cleavage by the short-armed lacZ ribozymes.

FIG. 8 is a photographic representation showing expression of long and short-armed lacZ ribozymes in S. pombe transformants. Cells transformed with plasmids containing lacZ ribozyme genes showed expression of the respective ribozymes with comparable steady-state levels.

FIG. 9 is a graphical representation showing in vivo assay of long and short-armed lacZ ribozymes. The inclusion of a hammerhead ribozyme in the short 5' lacZ antisense RNA resulted in differential elimination of antisense RNA-mediated suppression. The short-armed lacZ ribozymes did not significantly reduce β-galactosidase activity.

Figure 12A:
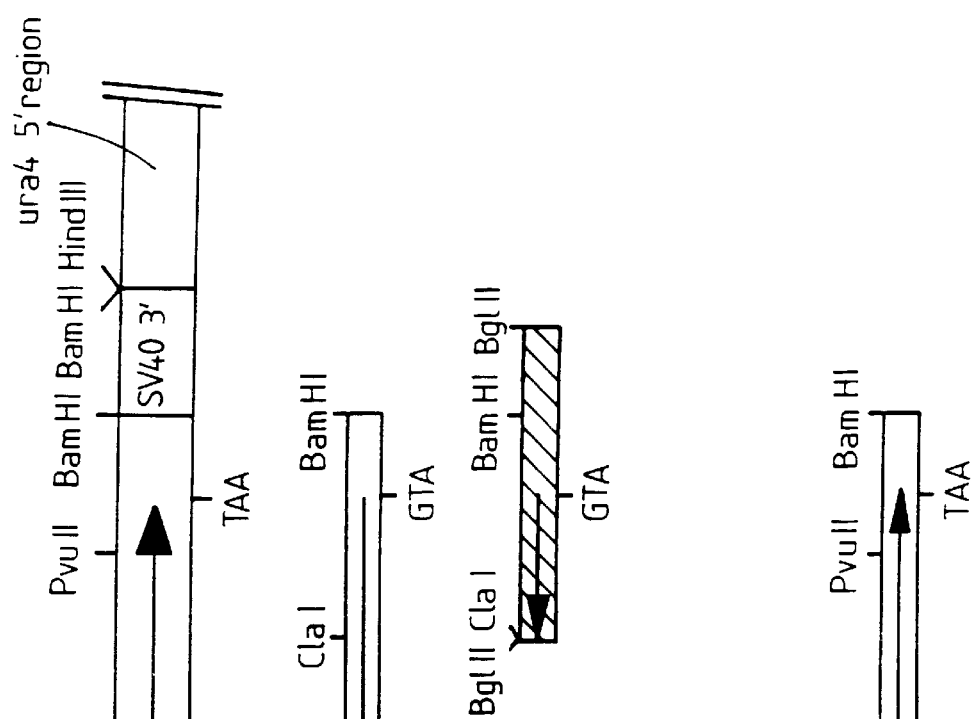

FIGS. 12(A) and 12(B) are a schemmatic diagram showing the lacZ target gene and antisense and control plasmids.

Figure 13A:
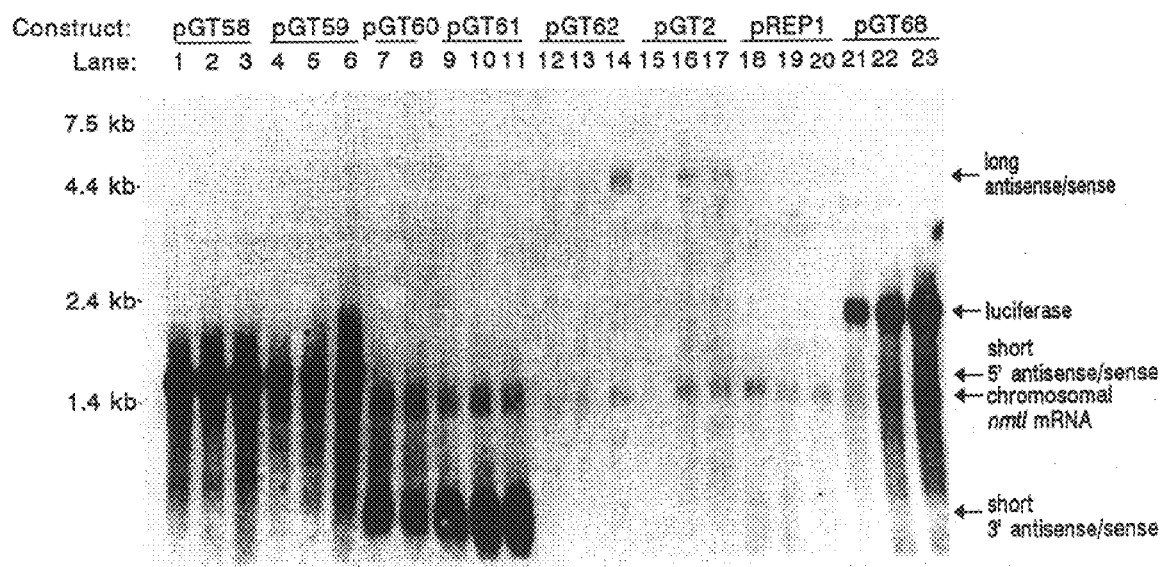

FIG. 13A is a photographic representation of a Northern blot of total RNA isolated from KC4-6 cells transformed with each of the expression vectors shown in FIG. 12.

Figure 13B:
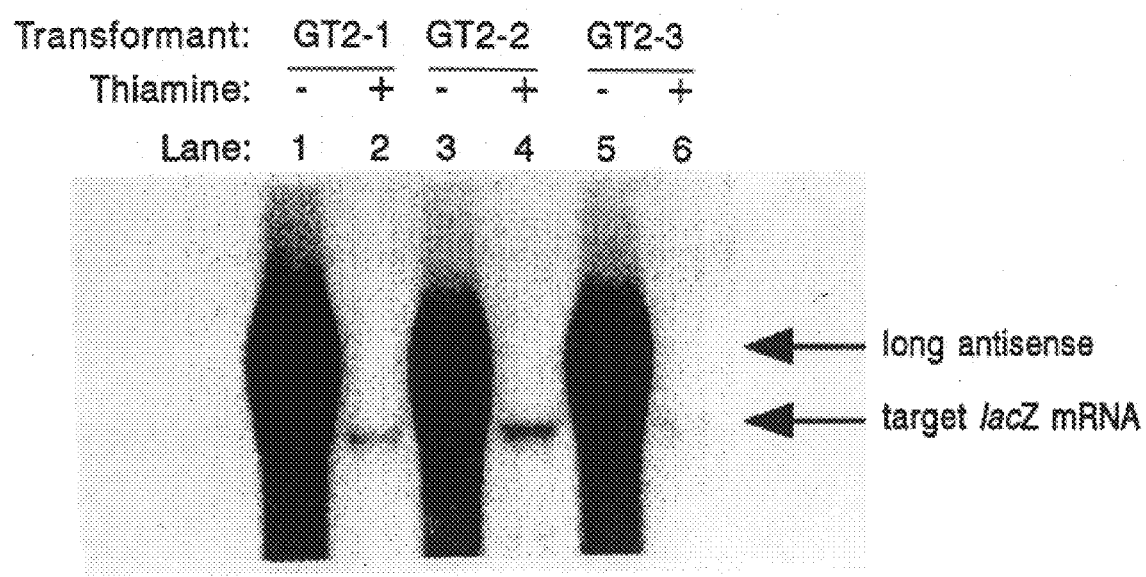

FIG. 13B is a photographic representation of a northern blot of total RNA isolated from independent pGT2 transofrnants of strain KD4-6 (GT2, GT2-2 and GT2-3) grown in the presence (+) and absence (−) of 4 μM thiamine.

Figure 14:
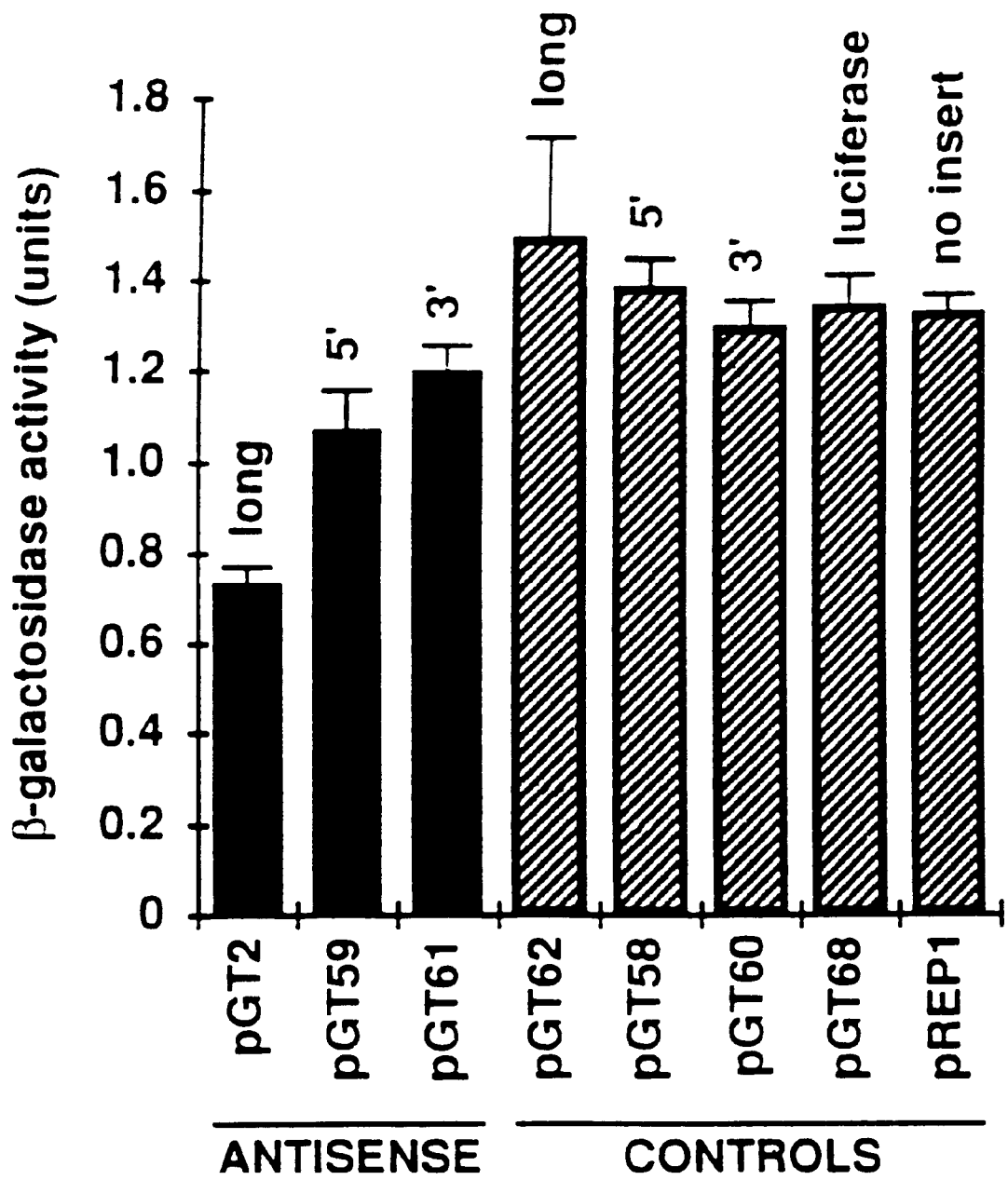

FIG. 14 is a graphical representation showing reduction of β-galactosidase activity in lacZ antisense transformants.

FIGS. 15A–D are graphical representations showing that reduction in β-galactosidase activity by long lacZ antisense RNA is transcription-dependent. The middle panel summarizes the experimental design. Single colonies from three independent transformants of pREP1 and pGT2 were split and streaked onto (A) EMM+U (nmt1 promoter ON) or (B) EMM+TJI+U (nmt1 promoter OFF). In the second stage of the experiment (C) cells of each transformant on EMM+U were streaked to EMM+THI+U (nmt1 promoter OFF), and (D) cells of each transformant growing on EMM+THI+U were streaked to EMM+U (nmt1 promoter ON). Each sample in the histogram epresents the average of three independent transformants and the standard deviation is indicated by the error bars.

Figure 16:
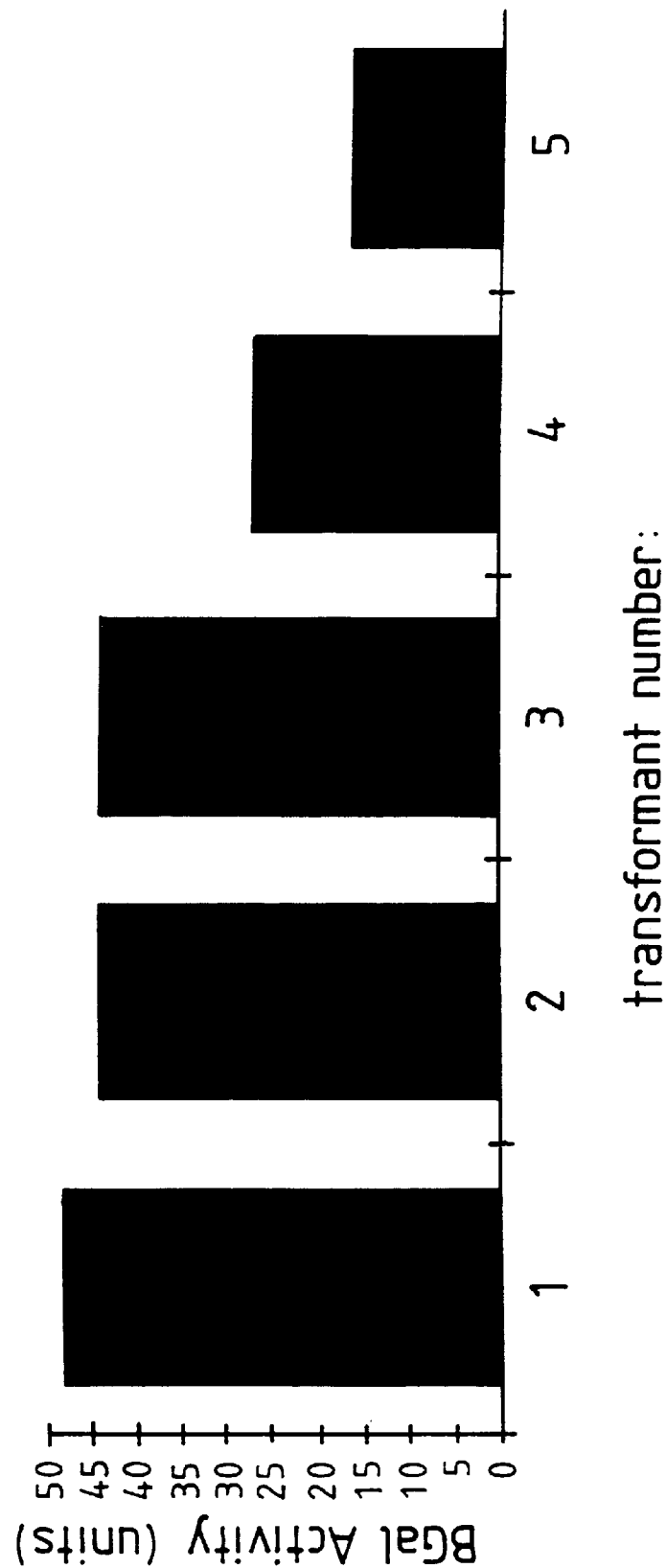

FIG. 16 is a graphical representation showing the role of antisense RNA level on the suppression of the lacZ gene in RB3-2.

EXAMPLE 1

CONSTRUCTION OF pREP1

Plasmid pREP1 was constructed according to Maundrell, K., *J Biol. Chem.* 265: 10857–10864, 1990.

EXAMPLE 2

INHIBITION OF β-GALACTOSIDASE EXPRESSION

The present invention is conveniently exemplified using the β-galactosidase gene from *E. coli* as a target. This gene has the advantage of having a well characterised and easily detected cellular phenotype. Cells expressing β-galactosidase turn blue or become fluorescent when incubated with appropriate substrate analogues. This permits rapid visual identification or fluorescence-activated cell sorting and quantitation of cells expressing the gene. Moreover, there are very sensitive solution enzyme assays which permit accurate quantitative assessment of β-galactosidase expression using extracts of cell populations. β-Galactosidase has been used as a reporter gene in molecular biology experiments in many systems and is an excellent building block for gene fusions. β-Galactosidase can be used to tag a wide variety of cellular or viral genes and monitor their expression and physiology.

Figure 1A:
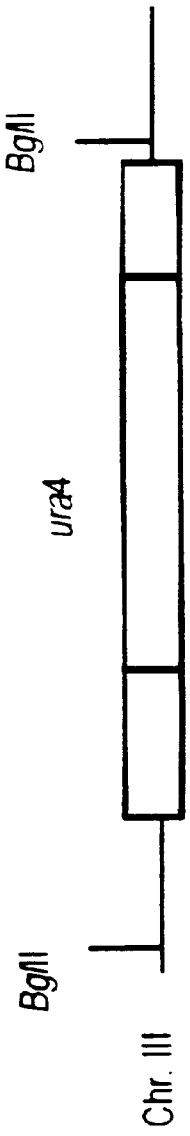
Figure 1B:
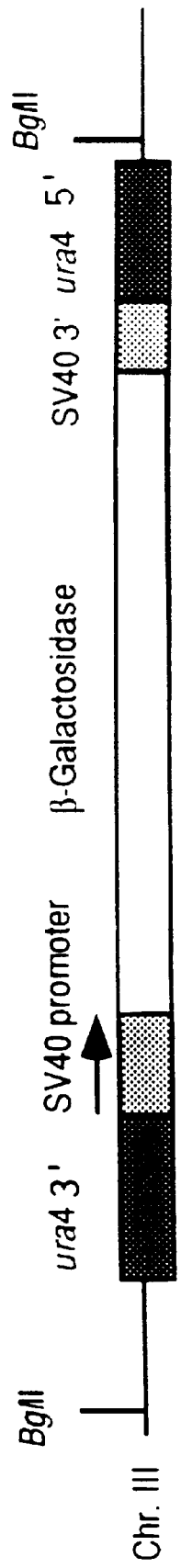
Figure 1C:
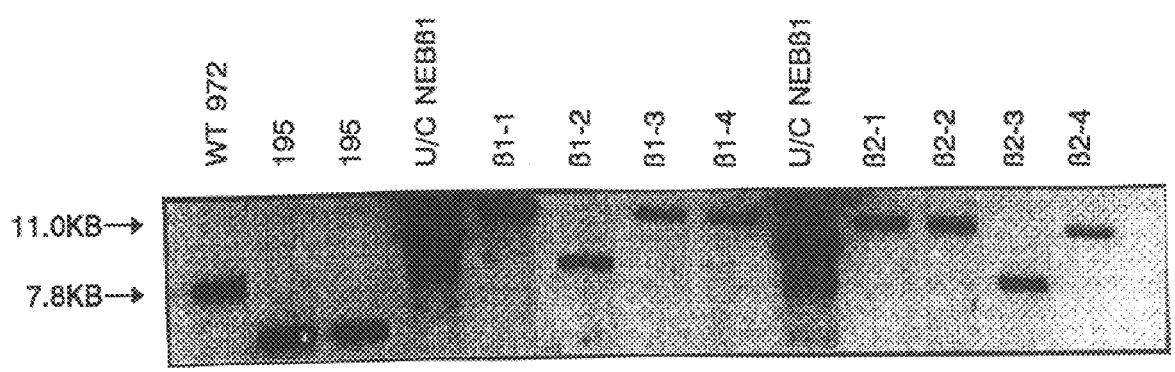

In accordance with an exemplified embodiment of the present invention, the β-galactosidase gene has been put under the control of the SV40 early promoter. This has been integrated into the ura4 gene locus of *S. pombe* to create KC4-6, a stable constitutive strain of yeast expressing β-galactosidase. FIG. 1 shows a diagram of the wild-type ura4 locus at the top. The middle of the diagram is a representation of the integrated β-galactosidase gene and the bottom of the figure shows a Southern blot confirming the integrity of the chromosomal β-galactosidase gene in β2-1 (the strain used to derive KC4-6) and other similar strains. Clearly, other target genes may be inserted into the ura4 or another locus. Furthermore, the target gene may also be expressed from extra-chromosomal episomes or plasmids.

Figure 2A:
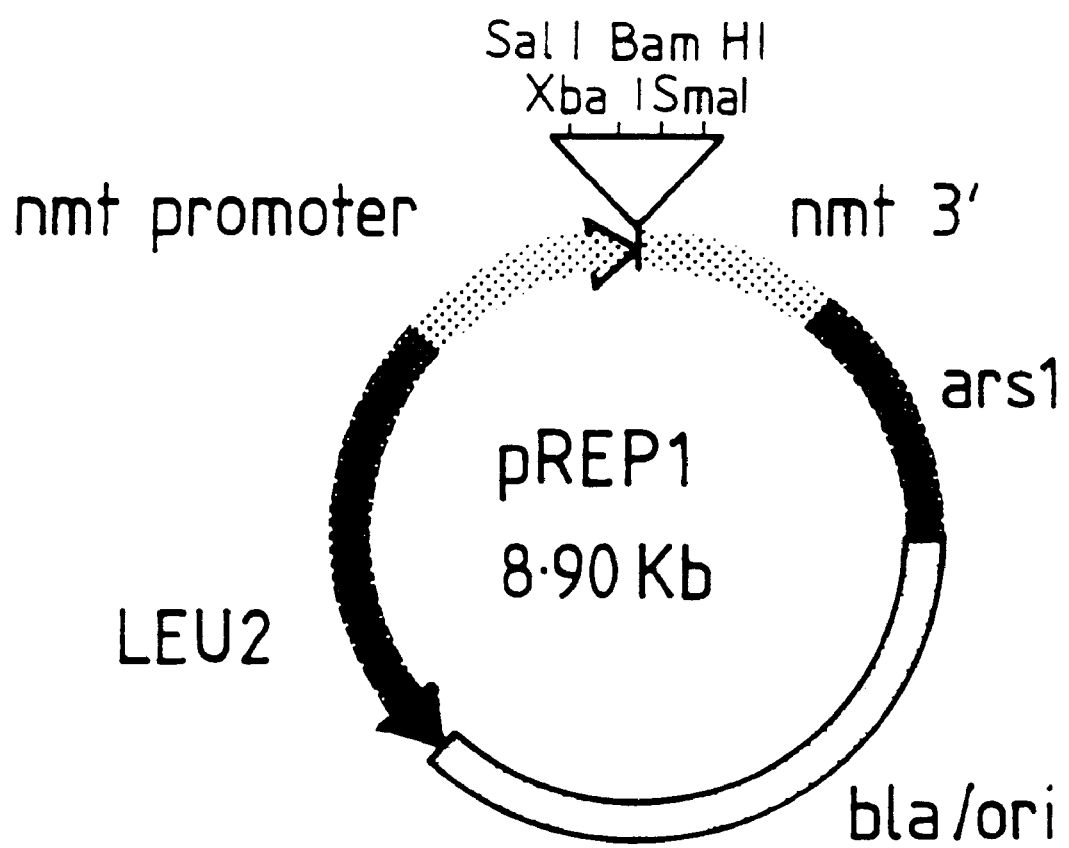
Figure 2B:
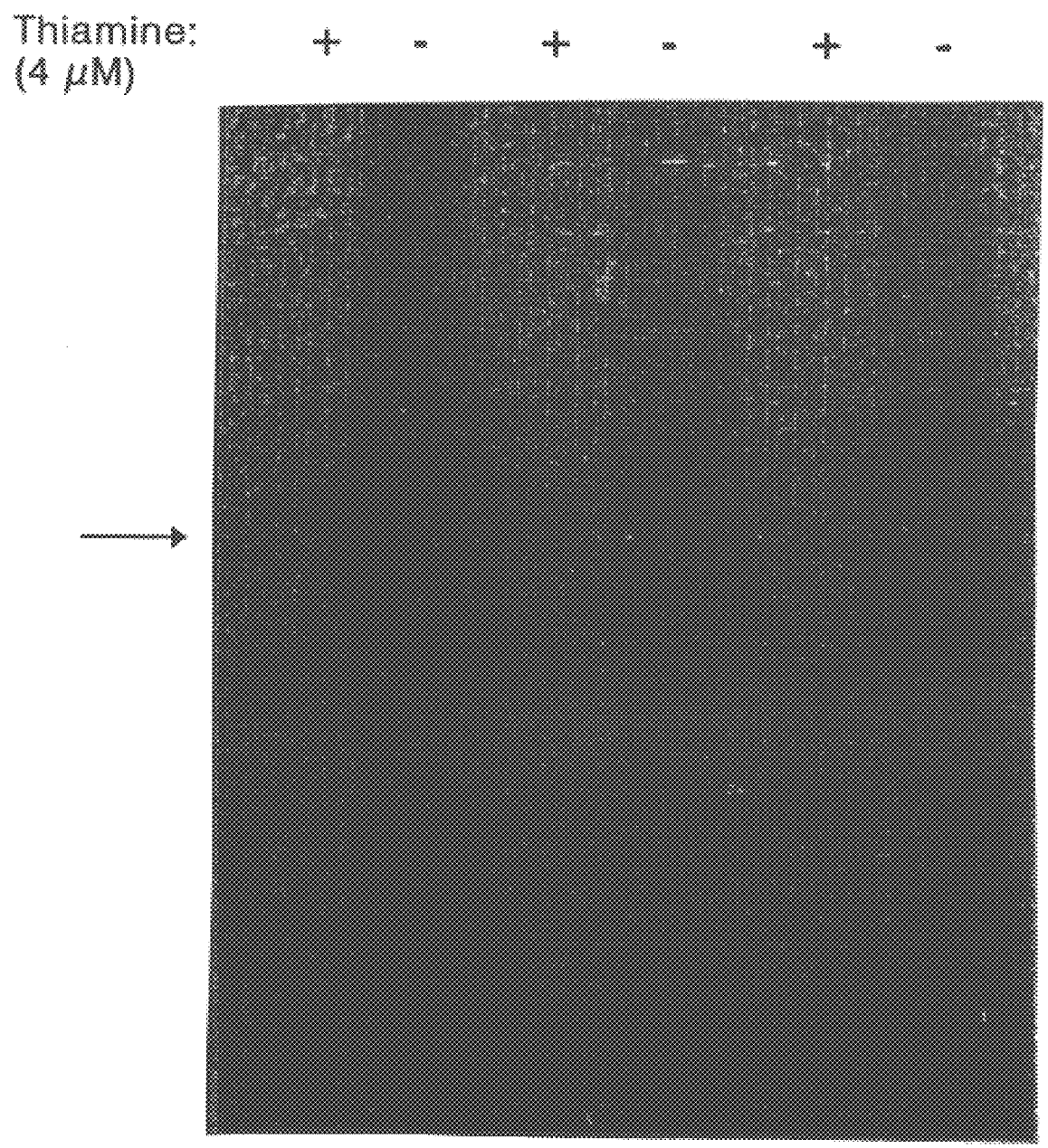

Regulated expression of antisense genes has been achieved using episomal vectors with conditional promoters. FIG. 2 shows the structure of the vector pREP1 which contains the nmt (no message in thiamine) promoter. Sequences cloned downstream of this promoter are expressed at a very high level when grown in the absence of thiamine. Transcription is almost undetectable in the presence of thiamine. The right hand panel in FIG. 2 shows a representative RNA blot probed with a double stranded β-galactosidase probe which documents the high level of expression of antisense β-galactosidase RNA in the absence of thiamine (in the "−" lanes). In the presence of thiamine ("+" lanes), only the target, sense-orientation β-galactosidase transcript is detected. Other expression systems may also be used.

FIG. 3 shows diagrams of the antisense gene constructs used in the present disclosure. Antisense or reverse orientation fragments encompassing the protein-coding domain (long), the 5' end of the gene and the 3' end of the gene were each cloned behind the nmt promoter in the pREP1 expression plasmid. A set of plasmids were constructed as controls for potential non-specific effects on the pattern of gene expression, cell growth or β-galactosidase levels. These included sense orientation fragments of β-galactosidase from the coding region (long), the 5' end and the 3' end as well as a sense oriented fragment from a non-related reporter gene luciferase. A frame shift mutation was inserted in the long sense control gene to eliminate the production of spurious additional β-galactosidase. Other fragments of the β-galactosidase gene or other reporter and target genes may also be used in such a system.

Figure 4B:
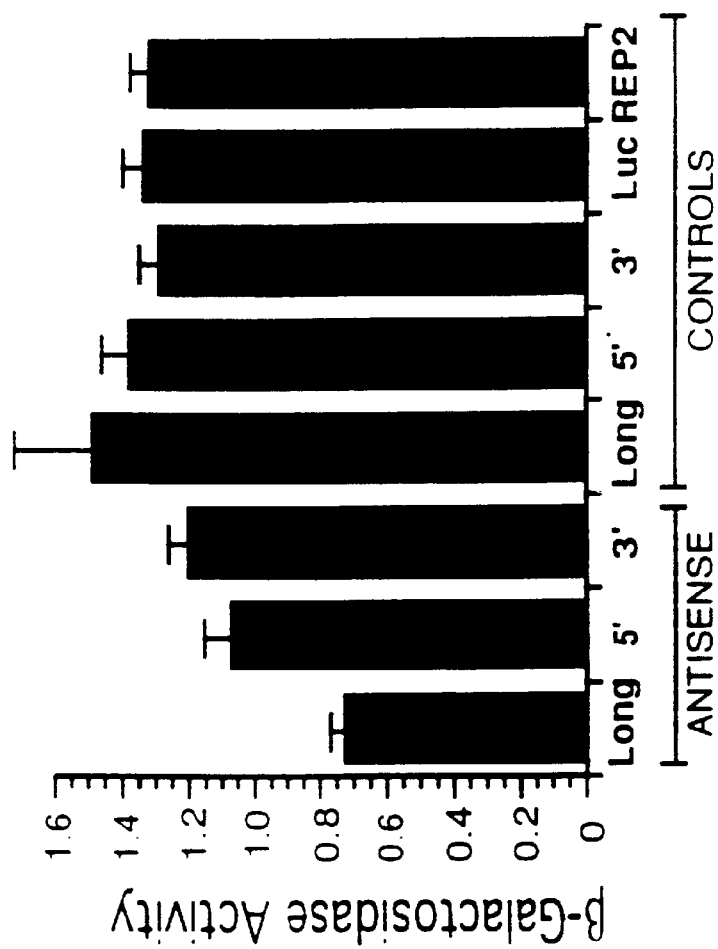
Figure 4A:
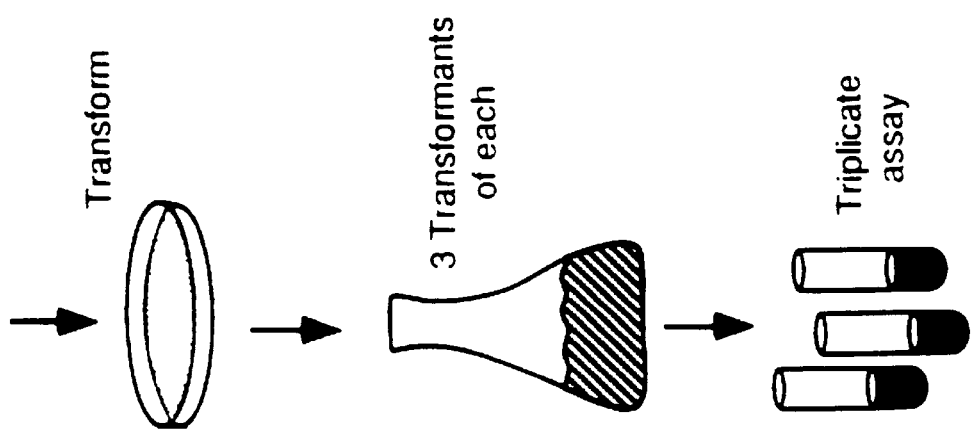
Figure 5C:
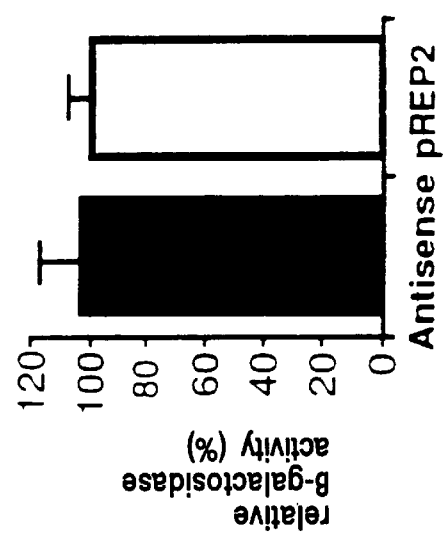
Figure 5D:
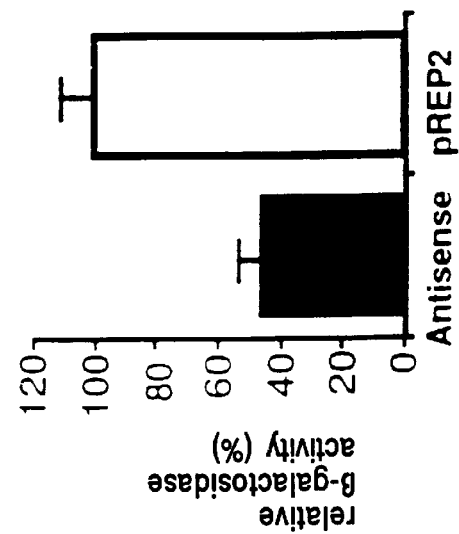
Figure 5E:
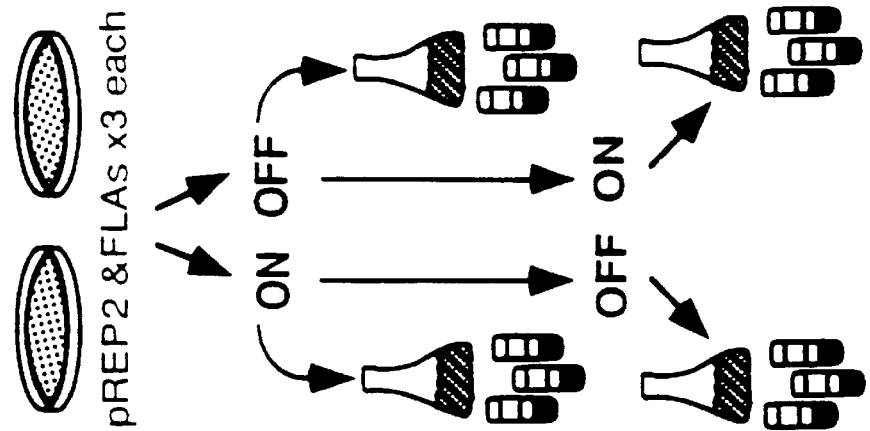
Figure 5A:
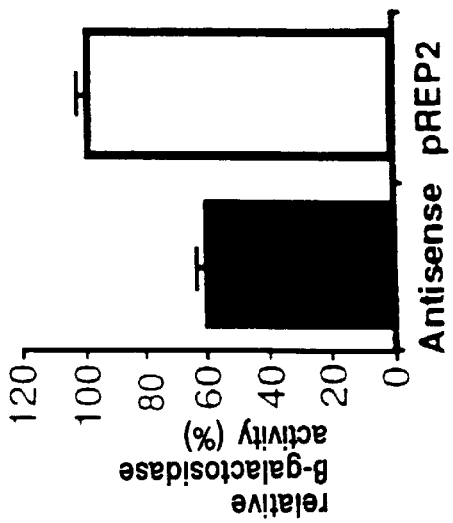
Figure 5B:
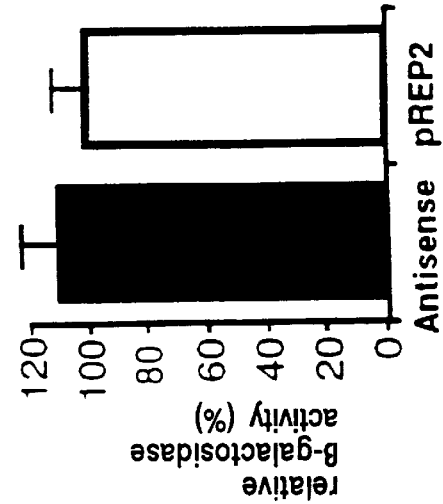

The antisense gene expression vectors are introduced into the β-galactosidase-expressing target strain by electroporation although other methods of gene transfer may also be used. The cells are grown in media lacking thiamine to promote expression of the antisense genes. Log phase cells at a constant cell density are assayed for β-galactosidase activity using solution assays and the chromophore substrate O-nitrophenol β-D-glactropyranside (ONPG). Reporter enzyme levels are determined by observing the OD 420 nm after 30 minutes. Multiple independent transformants have been assayed in triplicate and the results from several experiments are compiled in FIG. 4. The schematic diagram on the left depicts the protocol for the experiment and the histogram indicates the average level of β-galactosidase activity in cells transformed with each of the antisense constructs. The error bars indicate the standard deviation of the population. It can be seen that the parental pREP1 plasmid and all of the plasmids having sense orientation gene fragments (labelled controls) have within the experimental error of this system, the same level of β-galactosidase activity. *S. pombe* cells containing the long antisense plasmid reproducibly show a 45% reduction in β-galactosidase level while the 5' and 3' antisense cells show a 20% and 10% reduction, respectively. This experiment is the first documentation of antisense gene suppression in yeast cells and demonstrates the relative activity of the long, 5' and 3' fragments for artificial gene regulation.

To confirm that the observed inhibition is due to the expression of the antisense β-galactosidase RNA a series of experiments documented in FIG. 5, was performed. Parallel cultures of the long antisense strain and the control pREP1 strain were alternately grown in thiamine-containing medium to inhibit antisense production and then in thiamine-free medium to "turn on" antisense expression (right side of middle diagram in FIG. 5). Reciprocal experiments were performed where cultures were grown in thiamine-free and then in thiamine-containing medium (left side of middle diagram FIG. 5). As shown in the flanking histograms, cells which showed significant inhibition of β-galactosidase in the absence of thiamine showed no inhibition when grown in thiamine (left two histograms in FIG. 5) while cells which showed no inhibition of β-galactosidase when grown in thiamine showed approximately 55% inhibition (right two histograms in FIG. 5) when grown in the absence of thiamine (conditions which turn on antisense RNA transcription). These on-off/off-on experiments indicate that the long β-galactosidase plasmid produces transcript-dependent and sequence specific antisense suppression of the β-galactosidase gene in the KC4-6 type reporter gene strain of *S. pombe*. This system is valuable for genetic and biochemical explorations of artificial gene regulation technology.

From this, it is clear that one skilled in the art can now develop and use gene inactivation methods to inhibit gene activity in *S. pombe*. The present demonstration shows utility for antisense RNA transcripts but it will be appreciated by persons skilled in the art that it is applicable to other genes, synthetic antisense and ribozyme oligonucleotides, triplex, RNA and protein decoys, sense co-suppression, transdominant mutant approaches, defective interfering RNAs and DNAs, etc. This system is also applicable to the identification and development of small molecule therapeutics and pharmaceutical formations. Furthermore, it is applicable to a disease model system. All that is required is simple genetic constructions and demonstration of assay tests for effects on gene activity.

One application of this technology is the rapid and reliable screening on large scale of gene inactivation approaches and combinations of them to determine effective constructs for application through genetic engineering and genetic manipulation in the human, medical, animal, plant and fermentation application areas.

EXAMPLE 3

CONSTRUCTION OF AN *S. POMBE* STRAIN EXPRESSING THE TARGET lacZ GENE AT HIGHER STEADY-STATE LEVELS COMPARED TO STRAIN KC4-6

Figure 6A:
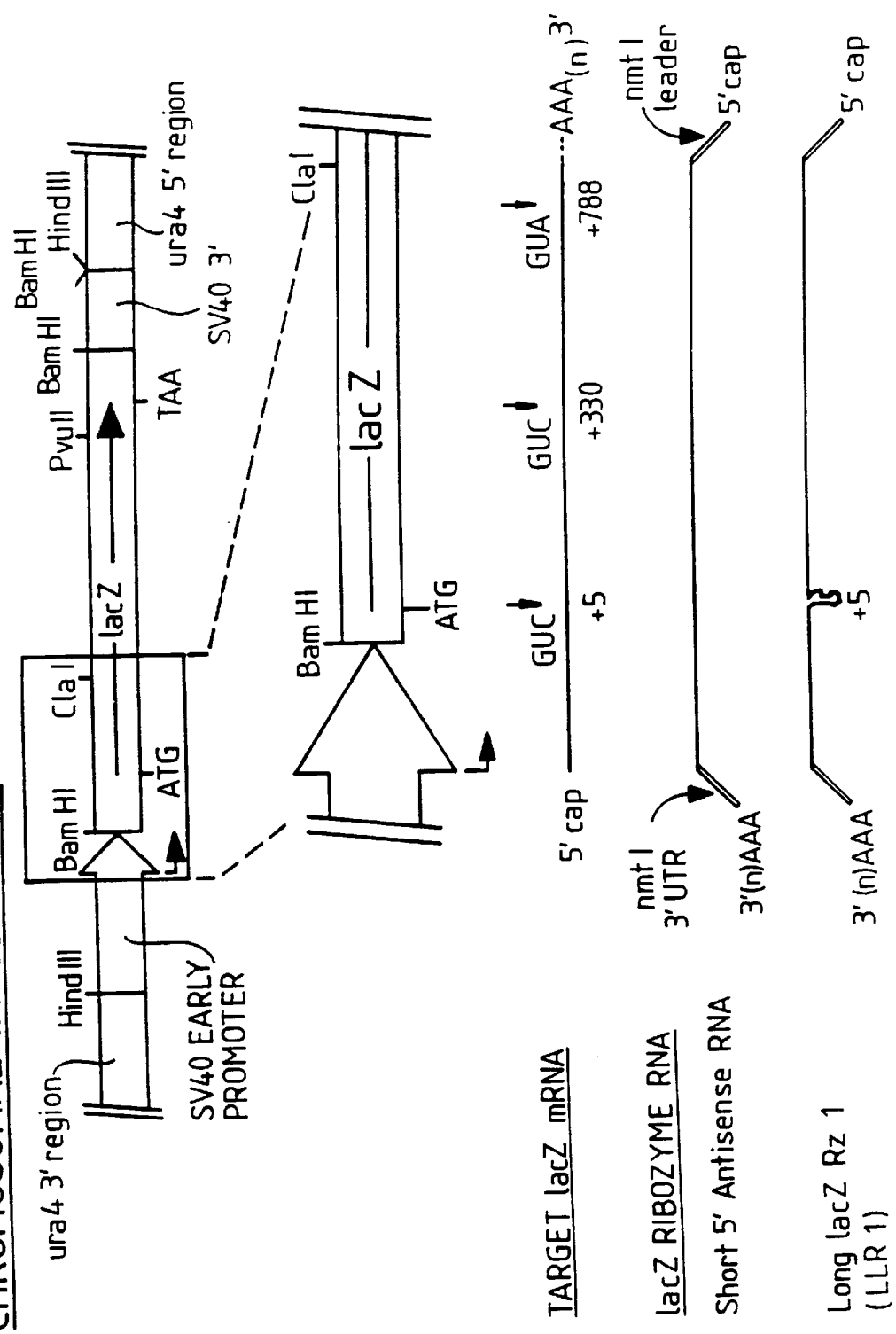
Figure 6B:
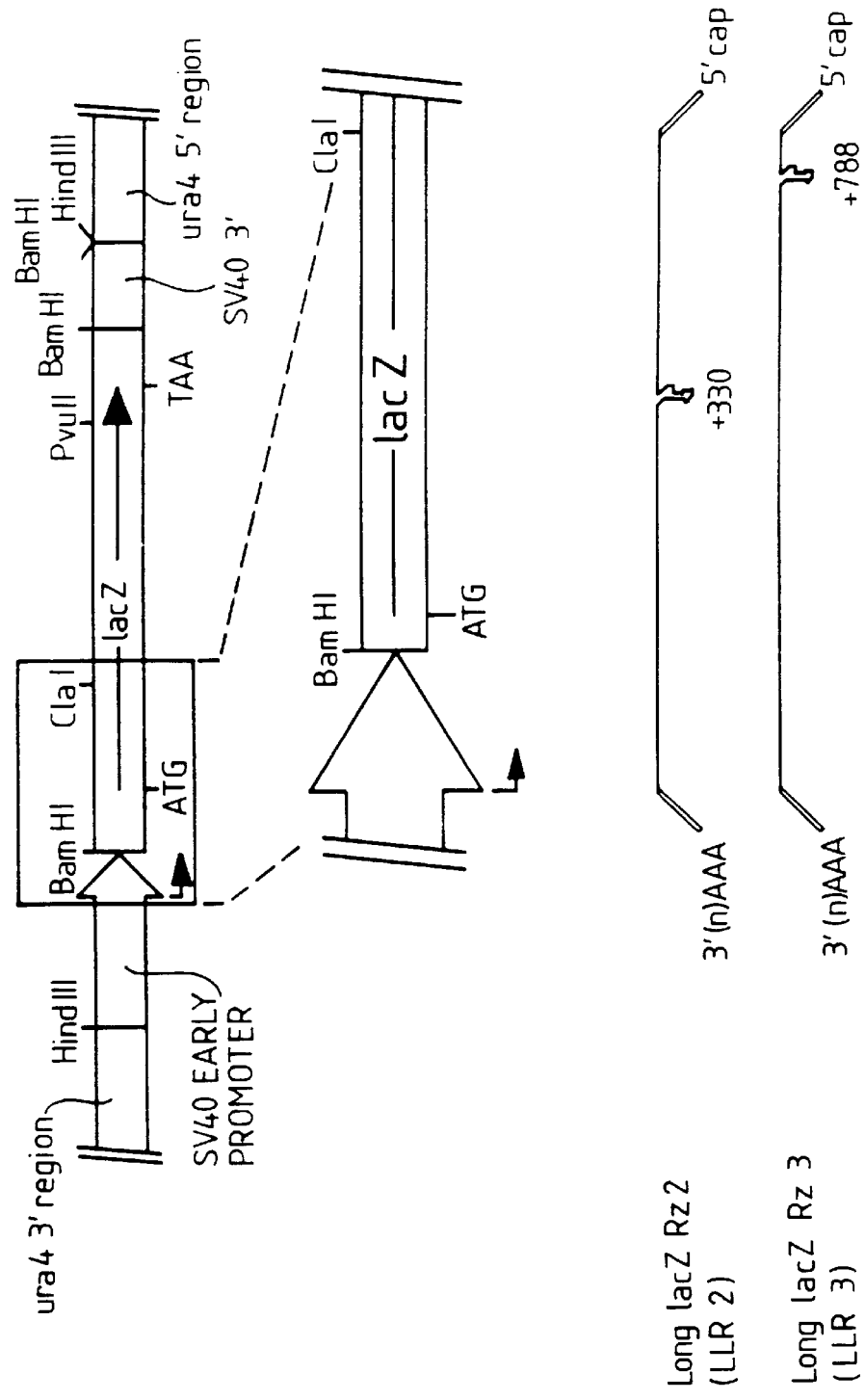
Figure 6C:
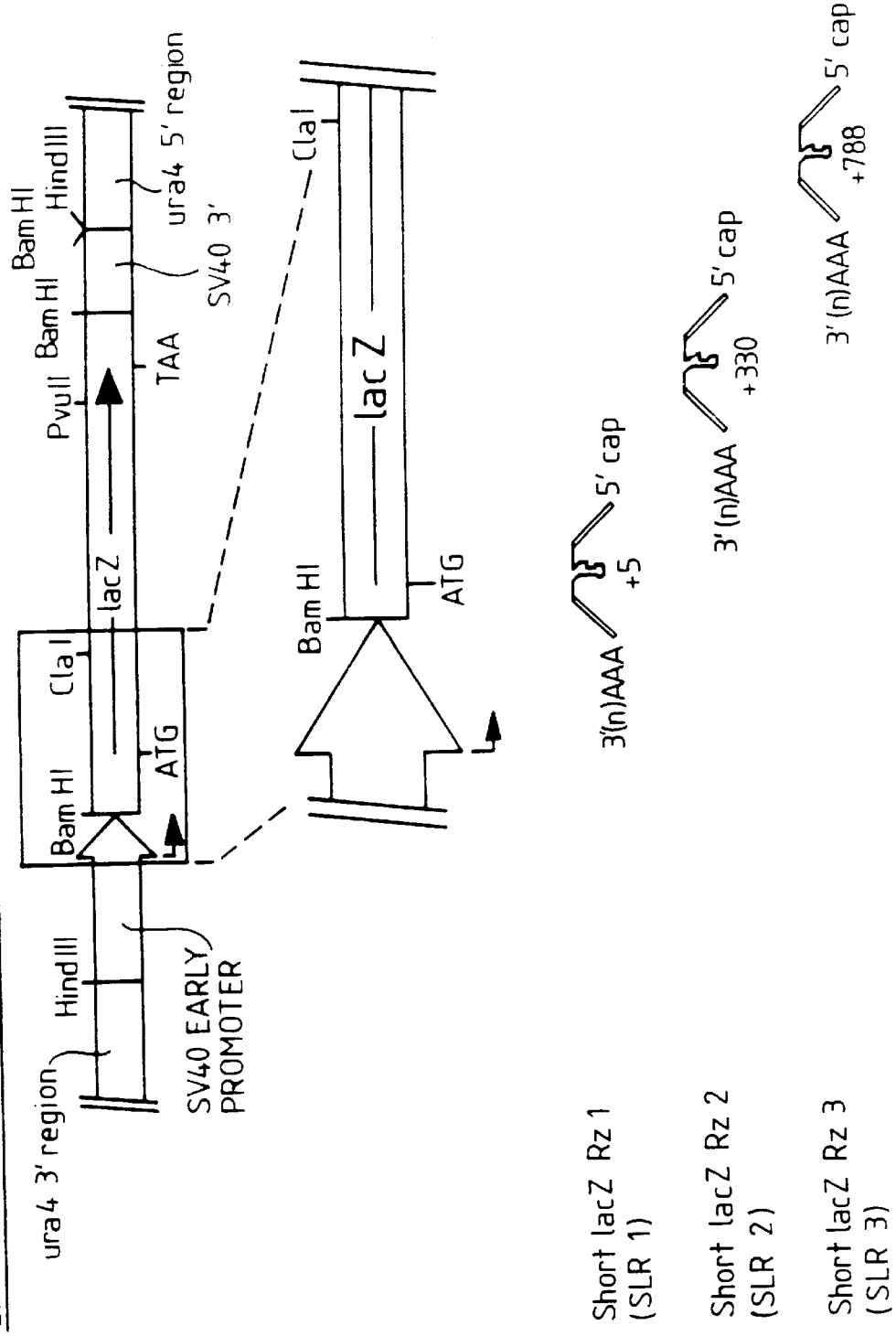
Figure 7A:
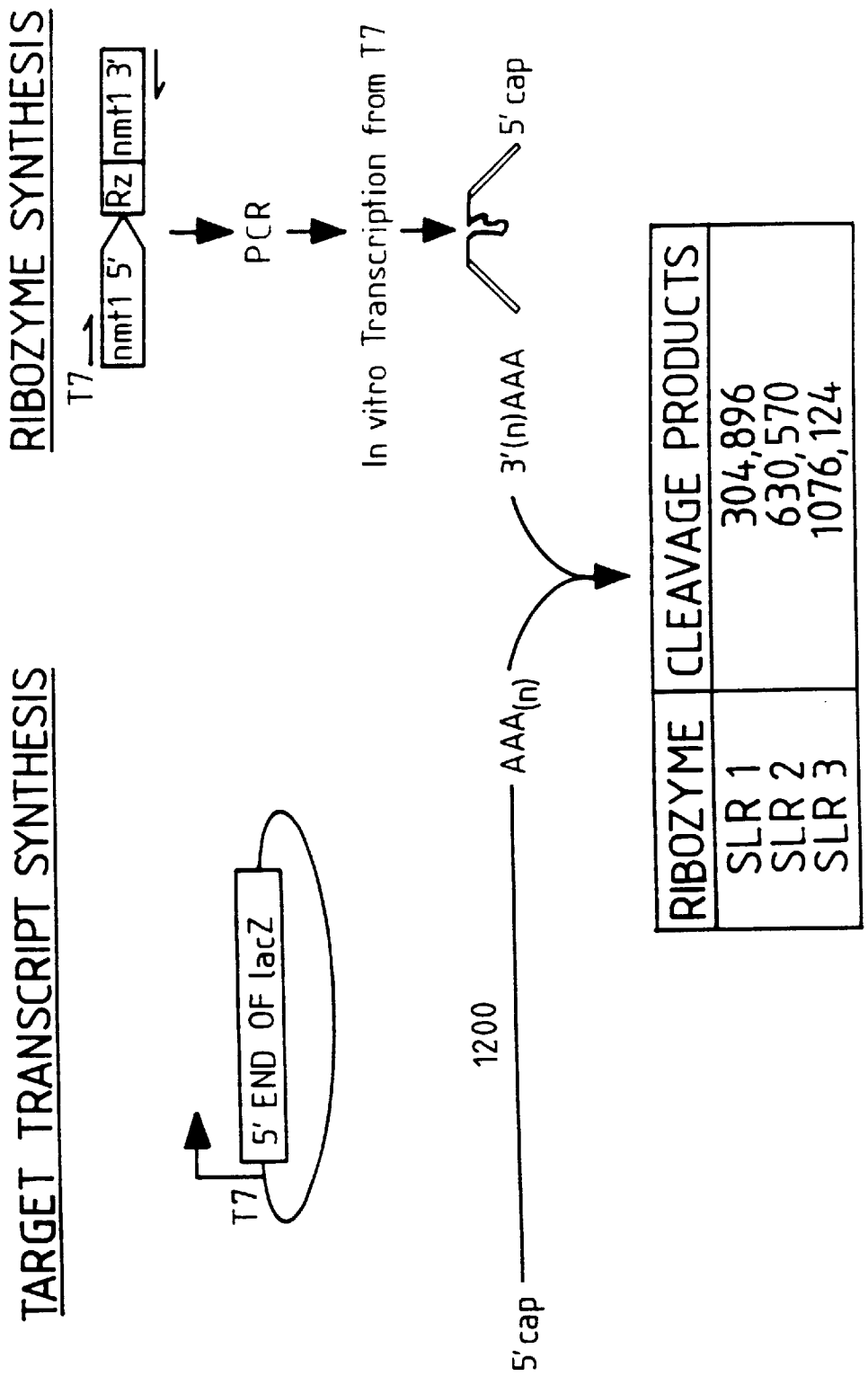
Figure 7B:
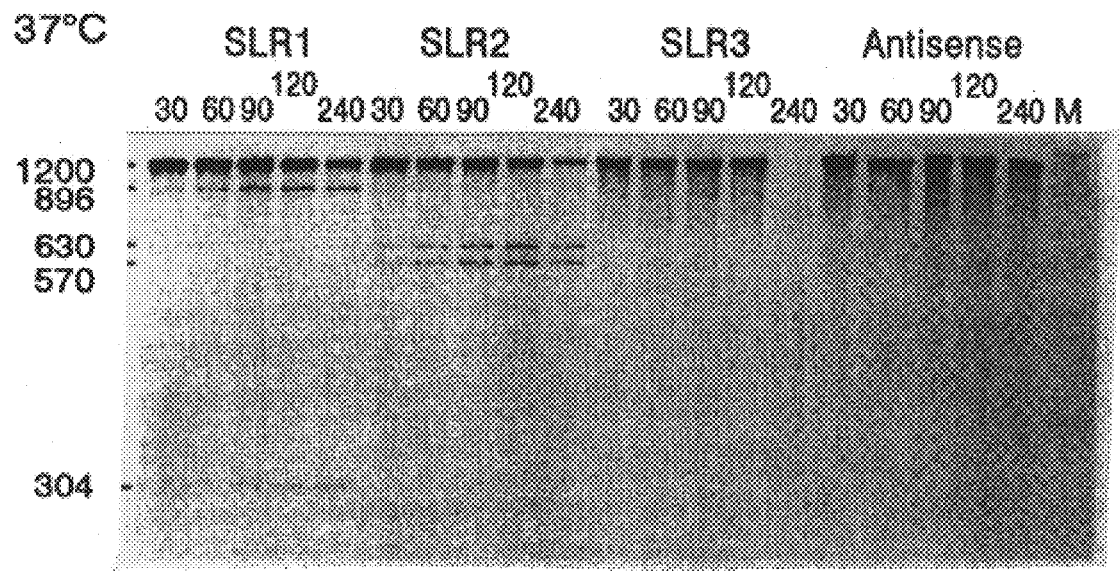
Figure 7C:
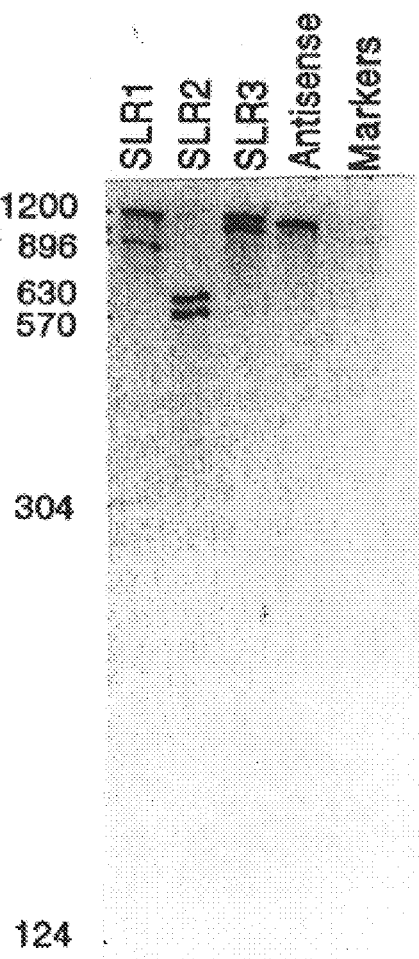
Figure 9:
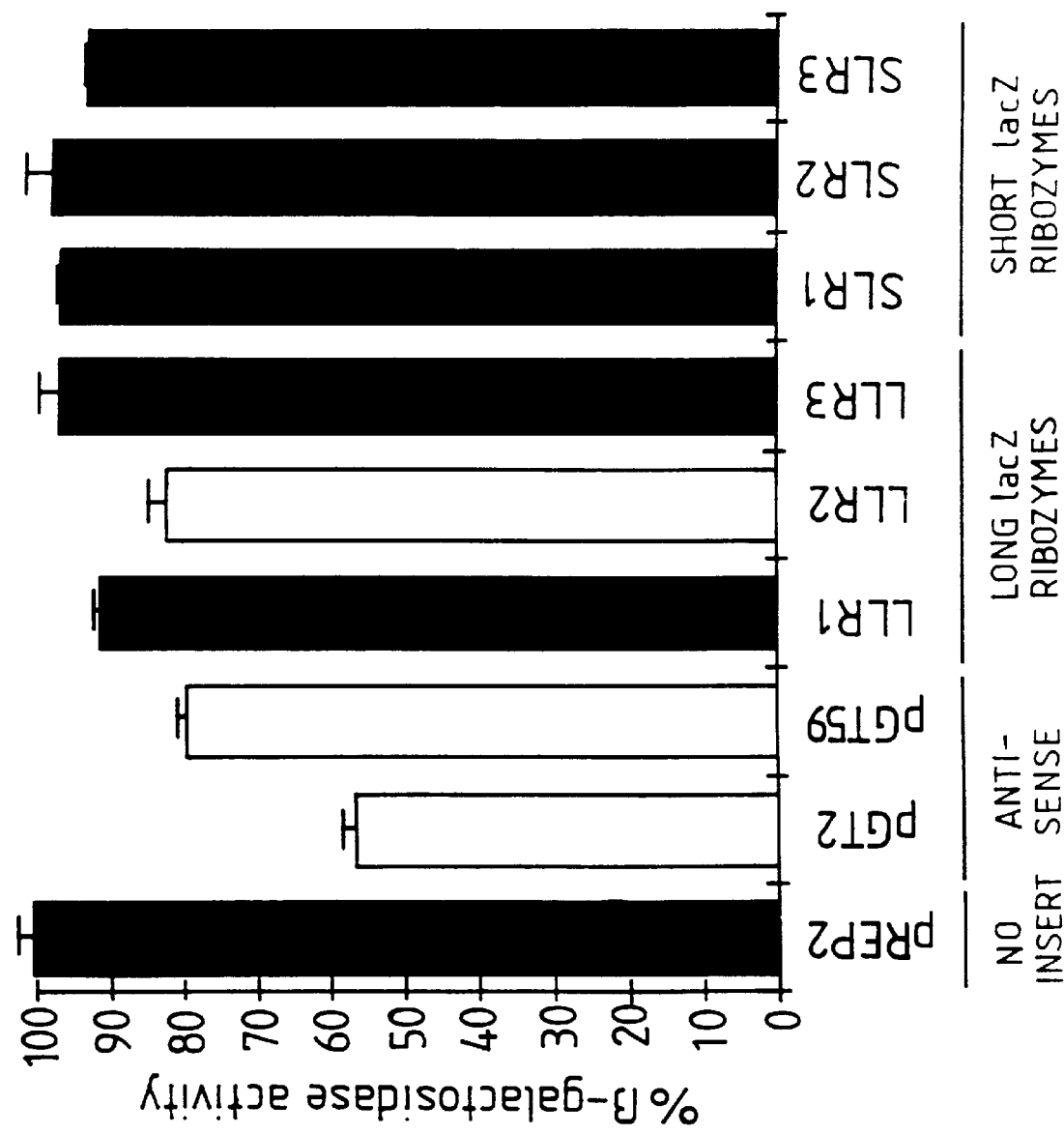
Figure 10:
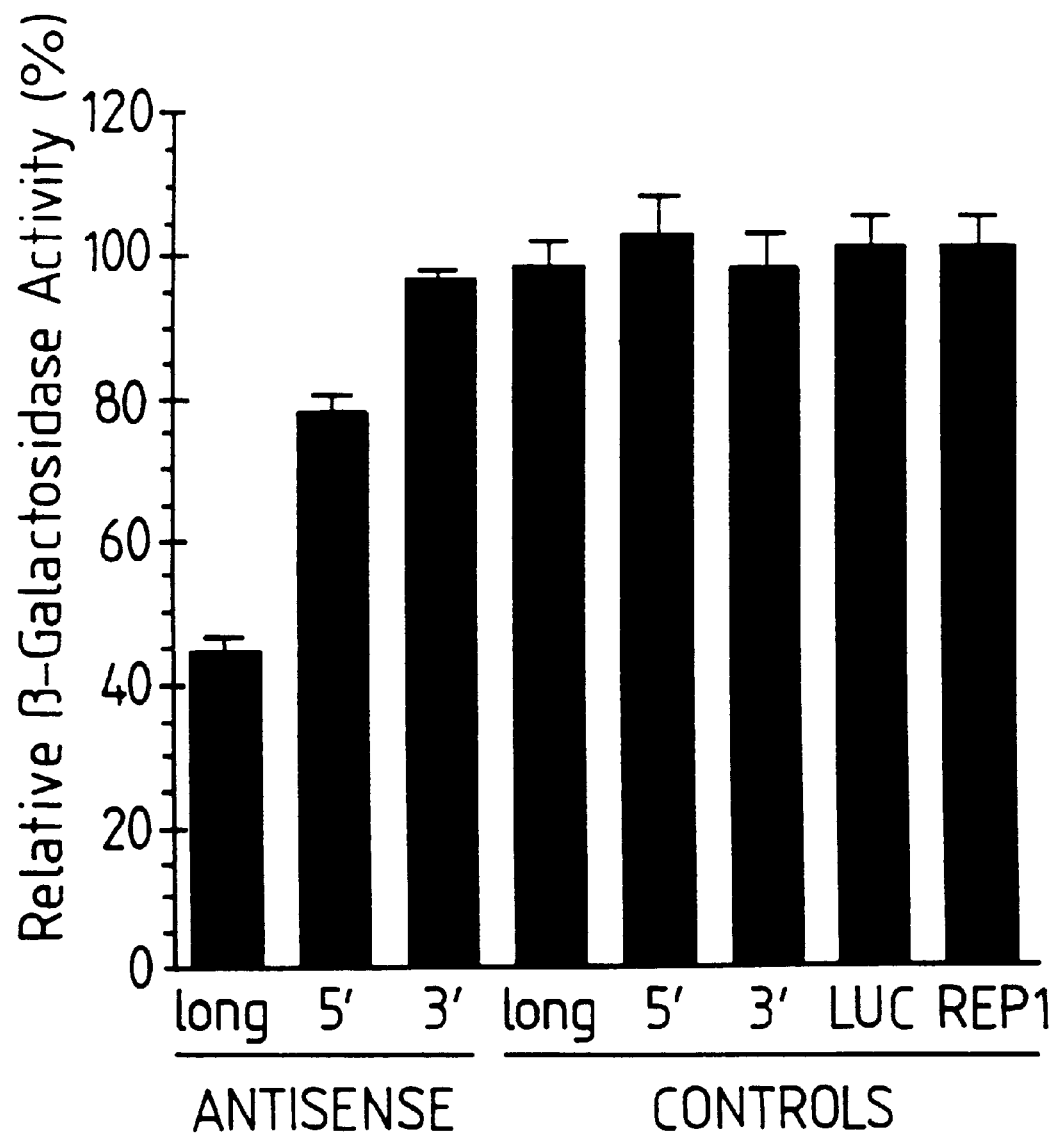
FIG. 10 is a graphical representation showing the antisense RNA inhibits gene expression in S. pombe strain RB3-2.
Figure 11:
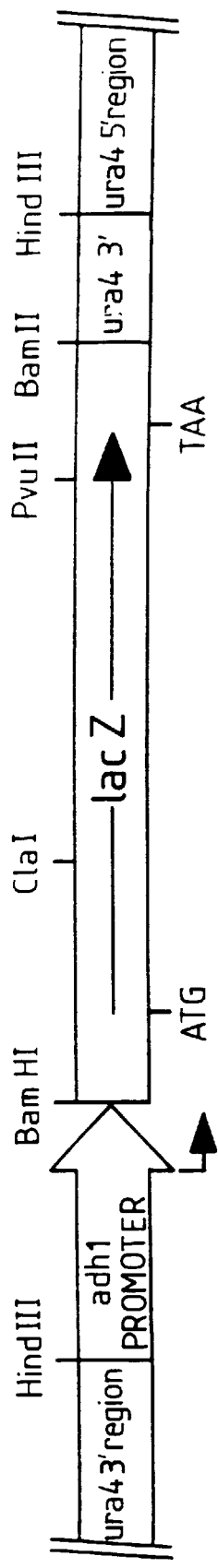
FIG. 11 is a diagrammatic representation showing that the ura4 locus in strain RB3-2 containing the adh1 promoter-β-galactosidase-ura4 3' expression cassette.

The β-galactosidase gene was placed under the control of the *S. pombe* adh1 promoter and the *S. pombe* ura4 3' processing region. This adh1 promoter-β-galactosidase-ura4 3' expression cassette was integrated at the ura4 locus of *S. pombe* to produce strain 599-2. FIG. 6 shows the integrated cassette at the ura4 locus in strain 599-2. This strain was crossed to a leu⁻ *S. pombe* strain to create the ascospore isolate RB3-2. This strain also contains the integrated adh1 promoter-β-galactosidase-ura4 3' expression cassette at the ura4 locus as indicated in FIG. 11 and exhibited a 20-fold increase in β-galactrosidase mRNA expression over KC4-6. Strain RB3-2 was transformed with the set of antisense and control plasmids represented in FIG. 3 (Example 2) and assayed for β-galactosidase activity. Multiple independent transformants were assayed in triplicate and the results for these experiments are summarized in FIG. 10. The protocol for this assay is as for FIG. 4 (Example 2). Cells of *S. pombe* expressing the long antisense RNA show a 55% reduction in β-galactosidase activity while the short 5' antisense RNA- and short 3' antisense RNA-expressing cells show a 22% and 4% reduction, respectively. As indicated, the control plasmid transformants exhibited similar levels of β-galactosidase activity to the pREP1 transformants. All RB3-2 transformants containing antisense or control plasmids have been shown to express the expected plasmid-derived RNA. The primary advantage of RB3-2 over KC4-6 is that single colonies of RB3-2 turn blue on X-gal medium. This reflects the higher level of expression of β-galactosidase in RB3-2 compared to KC4-6.

EXAMPLE 4

INHIBITION OF GENE EXPRESSION IN *S. POMBE* STRAIN RB3-2

The yeast strain RB3-2 described in Example 3 was tested for antisense inhibition of β-galactosidase. The results are shown in FIG. 10. Long and 5' antisense molecules were more effective at inhibiting β-galactosidase expression than 3' antisense molecule. A diagrammatic representation of the target gene in RB3-2 is shown in FIG. 11.

EXAMPLE 5

RELATIONSHIP BETWEEN BIOCHEMICAL ACTIVITY ASSAY AND PHENOTYPE READER

Analysis of lacZ expression can be completed by incubation of transformants on media containing Xgal. Xgal is a chromogenic substrate of the enzyme β-galactosidase and confers a blue phenotype to the colonies when hydrolysed. RB3-2 transformants described in FIG. 10 were plated on media containing 50, 100, 150 and 20 μg/ml of Xgal. After 5 days of growth an obvious reduction in the intensity of the blue colour of the strains expressing the full-length and 5' antisense was detectable when compared to the control transformed strain. This result demonstrates a relationship between lacZ expression and phenotype and illustrates how the *S. pombe* strain RB3-2 can be used in a genetic screen to identify genetic sequences, from libraries encoding random genetic sequences, that reduce the expression of the target lacZ expressing yeast strain when hydrolysed. Phenyl-β-d-galactropyranoside is a candidate compound for such a suicide substrate and is currently under investigation.

EXAMPLE 6

ANTISENSE MEDIATED REGULATION OF lacZ EXPRESSION IN *S. pombe*

Yeast Strains and Media

*Schizosaccharomyces pombe* strain 972 (h−) was used as the host for integration and expression of the *Escherichia coli* lacZ gene. Strains NCYC 1913 (h−, leul-32) and NCYC 1914 (h+, leul-32) were obtained from the National Collection of Yeast Cultures (AFRC Institute of Food Research, Norwich, UK). Yeast matings were performed according to standard procedures (Alfa et al., Experiments with fission yeast: A laboratory course manual. Cold Spring Harbor Laboratory Press, Cold Spring Harbor, N.Y., 1993). The transformation of *S. pombe* cells with episomal plasmid DNA or linearized plasmid DNA was carried out using electroporation (Prentice, H. L. *Nucleic Acids Res.* 20: 621, 1992). Gene replacement at the ura4 locus in *S. pombe* was achieved as described by Grimm et al., *Mol. Gen. Genet.* 215: 81–86, 1988.

Yeast cells were grown on standard YES medium (BIO 101 Inc., Vista, Calif.) or synthetic dextrose (SD) medium containing biological supplements (Rose et al., Methods in yeast genetics: A laboratory course manual. Cold Spring Harbor Press, Cold Spring Harbor, N.Y., 1990). Thiamine-free EMM medium (BIO 101 Inc., Vista, Calif.) was used to obtain maximum expression from the promoter in yeast transformants. Repression of transcription from this promoter was achieved by the addition of thiamine (Sigma) to EMM medium at a fmal concentration of 4 μM (Maundrell, K., *J Biol. Chem.* 265: 10857–10864, 1990). Conjugation and sporulation of *S. pombe* cells was performed using nutrient deficient ME agar medium (BIO 101 Inc., Vista, Calif.) (Moreno et al., *Meth. Enzymol.* 194: 795–823, 1991). To examine the blue colony colour of yeast integrants expressing the *E. coli* lacZ gene, cells were plated onto SD or EMM media buffered with potassium phosphate (to pH 7.0) and containing Xgal at final concentrations ranging from 50 to 200 μg/ml (Rose et al., Methods in yeast genetics: A laboratory course manual. Cold Spring Harbor Press, Cold Spring Harbor, N.Y., 1990).

Plasmids and Yeast Strain Construction

All standard DNA manipulations were carried out as described by Sambrook et al., 1989, Molecular Cloning: A laboratory manual. Cold Spring Harbor Laboratory Press, Cold Spring Harbor, N.Y. The *E. coli* lacZ gene under control of the SV40 early promoter and 3' processing signals was integrated into the *S. pombe* genome using ura4 flanking DNA sequences and homologous recombination at the wild type ura4 gene locus. The ura4 DNA sequences flanking the ura4 transcriptional unit were isolated from pCG5 (Prof. J. Kohli, University of Bern, Bern, Switzerland) as a 1.8 kb BamHI-EcoRI fragment (Grimm et al., *Mol. Gen. Genet.* 215: 81–86, 1988). This fragment was filled using the Klenow fragment of DNA polymerase and subcloned as a blunt end fragment into the HindII site of pNEB194 [a version of pNEB193] (New England Biolabs Inc., Beverly, Mass.) from which the region between the PstI and HindIII sites in the polylinker was deleted] to create pNEB 195. The lacZ expression cassette containing the SV40 early promoter, the *E. coli* lacZ gene and the SV40 early gene 3' processing sequence was subcloned from the plasmid pSVβ (Clontech Laboratories Inc., Palo Alto, Calif.). The EcoRI site 5' to the SV40 promoter in pSVβ was modified to include a HindIII site by inserting an EcoRI-HindIII-EcoRI adaptor. The above cassette was then subcloned as a HindIII fragment between the ura4 L 5' and 3' sequences in pNEB 195 to produce plasmid pNEBD2 with an orientation such that the SV40 early promoter was located adjacent to the ura4 3' fragment. A PacI-PmeI double-digest released the lacZ expression cassette flanked at either end by ura4 sequences. This fragment was used to transform *S. pombe* strain 972 (h–) and 5-FOA resistance was used to identify yeast transformants having undergone a disruption of the ura4 locus. Putative integrants were then characterized with respect to the structure of the ura4 locus and expression of the SV40 early promoter-driven lacZ gene. The structure of the integrated lacZ expression cassette at the ura4 locus in chromosome III of the *S. pombe* genome is depicted schematically in FIG. 12.

Plasmid pREP1 (Maundrell, 1990) was used as the expression vector for construction of lacZ antisense gene-containing plasmids and sense controls. All fragments used were subcloned into pREP1 at the unique BamHI site and are represented schematically in FIG. 12. The long lacZ BamHI fragment spans positions –56 to +3419 of the SV40 early promoter-driven lacZ expression cassette. In order to construct the long sense control plasmid, a frameshift mutation was introduced at base +909 in the lacZ BamHI fragment. The fragment was linearized with ClaI, filled and religated. The frameshift was confirmed by DNA sequencing and the lacZ BamHI fragment subcloned into pREP1 in the sense orientation relative to the nmt1 promoter. This plasmid was designated pGT62 and served as a control for pGT2 which contains the long lacZ BamHI fragment in the antisense orientation.

The short 5' and 3' lacZ fragments were generated using the polymerase chain reaction (PCR) and pNEBD2 plasmid DNA as a template. The primers used for amplification of the short 5' fragment were 5'-AAGAGATCTGCCTCTGAGCTATTCCAGAAGTAGTG-3' [SEQ ID NO:1] and 5'-AAGAGATCTCATCGATAATTTCACCGCCGAAAGGC-3' [SEQ ID NO:2]. For the short 3' DNA fragment these sequences were 5'-AAGAGATCTTCAGTATCGGCGGAATTACAGCTGAG-3' [SEQ ID NO:3] and 5'-AAGAGATCTCAATGTATCTTATCATGTCTGGATCC-3' [SEQ ID NO:4]. In each case a BglII restriction site was added to both the 5' and 3' ends of the amplified DNA fragments. The short 5' fragment spanned positions –299 to +912 while the short 3' DNA was located between +3093 and +3454 with the TAA stop codon of the lacZ gene at +3141. PCR amplified DNA was cloned into the BglII site in pSP72 (Promega Corp., Madison, Wisc.) and subcloned as BglII fragments into the BamHI site of pREP1 in both the sense and antisense orientations. The plasmid designations were as follows: pGT58 (short 5' sense), pGT59 (short 5' antisense), pGT60 (short 3' sense), and pGT61 (short 3' antisense). A non-sequence specific plasmid control pGT68, containing the luciferase gene, was constructed by linker ligating the StuI-BamHI fragment of pGEM-luc (Promega Corp., Madison, Wisc.) into pREP1.

DNA:RNA Isolation and Hybridization

Total genomic DNA was isolated from *S. pombe* cells using glass beads as described by Hoffman and Winston (1987) *Gene* 53: 659–667. These DNA samples were used for Southern analysis of chromosomal DNA and copy number analysis of plasmids. Yeast total RNA was purified using a standard procedures. Nucleic acid electrophoresis and hybridization were as described (Sambrook et al., Molecular Cloning: A laboratory manual. Cold Spring Harbor Laboratory Press, Cold Spring Harbor, N.Y., 1989) with the exception of Northern blots which were hybridized using Express Hybridization solution (Clontech Laboratories Inc., Palo Alto, Calif.). DNA used as probes included the long lacZ BamHI fragment and the 405 bp BamHI-PacI fragment from the nmtl 3' sequence in pREP1. All DNA probes used for hybridization were $^{32}$P-labelled using the Megaprime labelling kit (Amersham International, Amersham, UK). The radioactive hybridization signal was detected by autoradiography and quantified using a phosphorimager (Bio-Rad Laboratories, Hercules, Calif.).

β-Galactosidase Enzyme Assay

The enzyme activity of the *E. coli* lacZ gene-encoded product, β-galactosidase, was assayed using a cell permeabilization method (Ausubel et al., Current protocols in molecular biology. Green Publishing Associates and Wiley-Interscience, New York, 1987). For *S. pombe* strains 972 and NCYC 1913, $1 \times 10^8$ cells were assayed for β-galactosidase activity following growth of yeast transformants in EMM or EMM media containing thiamine to a cell density of $10 \times 10^7$ cells/ml. Triplicate assays were performed for each transformant and β-galactosidase units calculated according to the formula described in Ausubel et al., Current protocols in molecular biology. Green Publishing Associates and Wiley-Interscience, New York, 1987).

Results

In order to examine the suitability of fission yeast as a model system for the analysis of antisense RNA-mediated gene regulation, the *E. coli* lacZ reporter gene was chosen as a target. This gene offers the advantages of the availability of rapid and sensitive solution enzyme assays for the gene product β-galactosidase (Ausubel et al., Current protocols in molecular biology. Green Publishing Associates and Wiley-Interscience, New York, 1987) and confers a blue colony colour to *S. pombe* on medium containing the chromogenic substrate Xgal (Kudla *Nucleic Acids Res.* 16: 8603–8617, 1988). The *E. coli* lacZ gene was expressed at a low constitutive level in *S. pombe* placing it under control of the SV40 early promoter and 3' processing sequences. This mammalian viral promoter has been shown to finction effectively in *S. pombe* with transcription initiating from the precise site used in mammalian cells (Jones et al., *Cell* 53: 659–667, 1988). The lacZ gene expression cassette was integrated into *S. pombe* chromosome III to create a stable β-galactosidase-expressing strain. Integration was accomplished by replacement of the DNA sequence at the ura4 locus with the ura4-flanked lacZ expression cassette and identification of a stable integrant using 5-FOA selection (FIG. 12). The integrity of the chromosomally integrated single copy plasmid DNA was confirmed by Southern analysis on genomic DNA isolated from strain β2-1 (h–, ura4::SV40-lacZ) and the chromosomal structure of the ura4 locus of this strain is shown in FIG. 12. Expression analysis on this lacZ gene-containing strain revealed that the strain expressed lacZ mRNA and produced an average of 1.8 units of β-galactosidase per $10 \times 10^8$ cells assayed. To facilitate transformation with episomal expression vectors the leu1 mutation was introduced into β2-1 by crossing with NCYC 1914 (h+, leu1-32) and a random ascospore isolate designated KC4-6 (ura4::SV40-lacZ, leu1-32) was identified. This strain was shown to express β-galactosidase at levels similar to that of the parental strain β2-1.

All lacZ antisense genes were expressed from the episomal plasmid pREP1 (Maundrell, K. *J Biol. Chem.* 265: 10857–10864, 1990) using the conditional nmt1 promoter. This promoter is repressed in the presence of thiamine at concentrations greater than 0.5 μM and maximally derepressed in the absence of exogenous thiamine (Maundrell, K. *J. Biol. Chem.* 265: 10857–10864, 1990). A set of antisense genes were constructed to produce antisense RNAs of varying sizes complementary to different regions of the target message (FIG. 12). The long lacZ antisense gene was designed to produce an antisense RNA complementary to 56 bases of the 5' untranslated sequence, the entire coding region of the target mRNA and 288 bases of the 3' untranslated region. The shorter antisense genes were designed to produce RNA complementary to either the 5' or 3' ends of the lacZ mRNA. Control expression plasmids were constructed in order to examine non-specific effects of high level nmt1 promoter-driven transcription on β-galactosidase enzyme levels (FIG. 12). These controls included the sense-oriented fragments for each of the antisense genes and the firefly luciferase gene in the sense orientation (FIG. 12). The long lacZ sense control plasmid was prepared by introducing a frameshift mutation into the lacZ gene to eliminate β-galactosidase activity of any resultant gene product. β-Galactosidase enzyme assays on pGT62 plasmid transformants of strain NCYC 1913 (h–, leu1-32) confirmed that transcripts produced from the long sense control gene were not translated into active β-galactosidase.

The target strain KC4-6 was transformed with each of the plasmid constructs described above and three independent transformants were analyzed to detect RNA transcripts expressed from the plasmid-borne genes. Northern analysis was completed using an nmt1 3' processing region DNA fragment as a probe. All RNAs produced from the nmt1 promoter on pREP1 contain 144 bases of the nmt1 message at their 3' ends. FIG. 13A indicates that each of the transformants produced an RNA species of the expected size. Analysis of each RNA species relative to the chromosomally-encoded nmt1 mRNA indicated that the expression levels of all these RNAs were similar. FIG. 13B shows that the expression of lacZ antisense RNA is conditionally dependent on thiamine and the expression level of long lacZ antisense RNA, as for all the antisense RNAs, is 20-fold greater than that of the target lacZ mRNA.

β-Galactosidase enzyme assays were used to monitor the effect of antisense RNA synthesis on target lacZ gene expression (Ausubel et al., Current protocols in molecular biology. Green Publishing Associates and Wiley-Interscience, New York, 1987). Three independent transformants for each plasmid construct were grown in thiamine-free medium to derepress the nmt1 promoter (FIG. 14). Cells of *S. pombe* expressing the long lacZ antisense RNA showed a 45% reduction in β-galactosidase activity, while cells expressing the short 5' or short 3' complementary transcripts produced 20% and 10% less β-galactosidase activity, respectively. In contrast, all transformants containing plasmids with the sense-orientated gene fragments exhibited levels of β-galactosidase activity comparable to the pREP1 transformants. This suggests that the decrease in β-galactosidase activity observed was due to the presence of lacZ antisense RNA and was not due to non-specific interference with gene expression or cell physiology.

Figure 15:
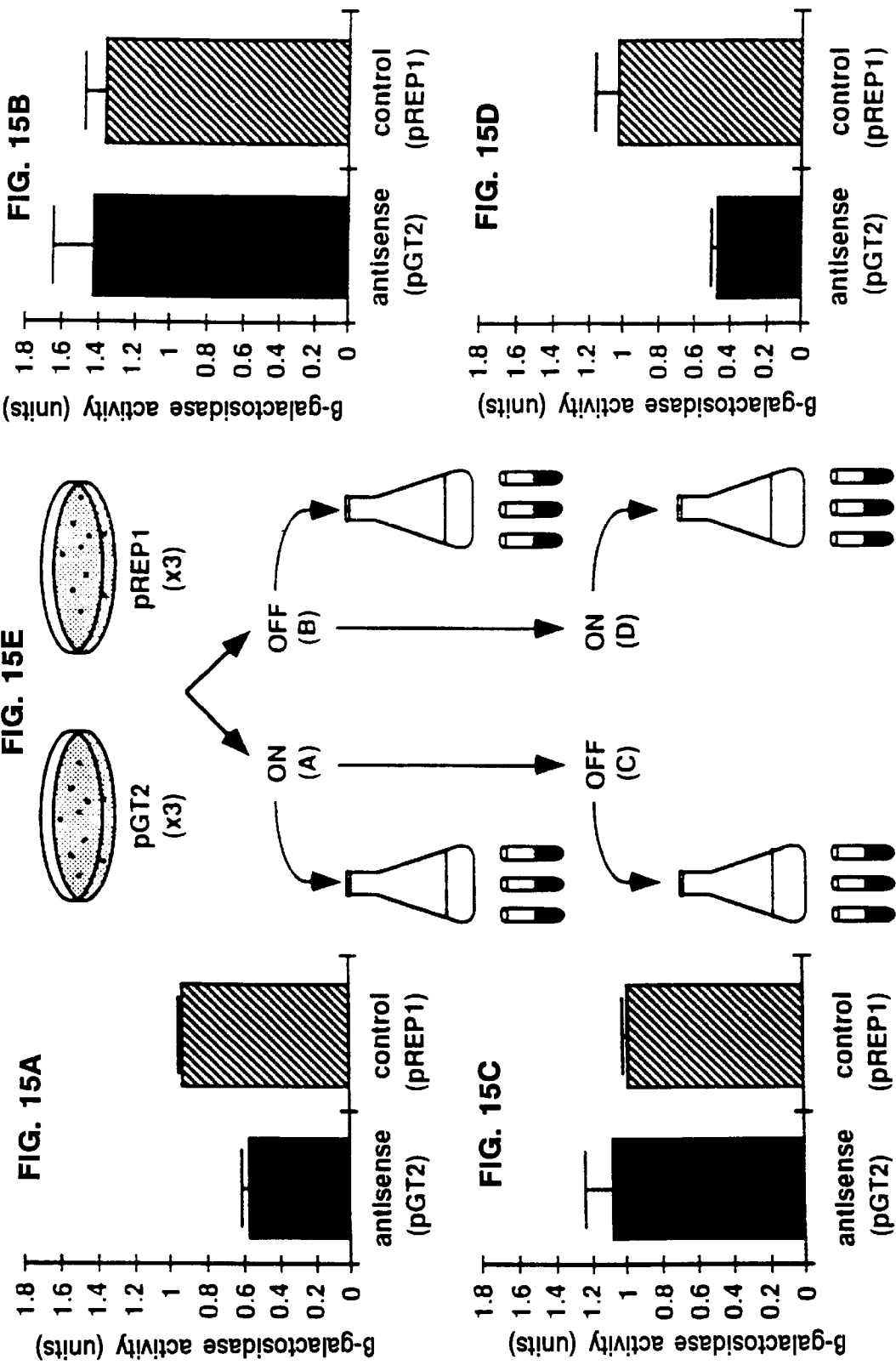

To confirm that the observed reduction of β-galactosidase activity was dependent on lacZ antisense RNA transcription, yeast transformants were grown under conditions that would repress or derepress the nmt1 promoter prior to assaying for β-galactosidase activity. Independent transformants, containing either control plasmid pREP1 or the long lacZ antisense plasmid pGT2, were initially grown on thiamine-free medium to permit antisense RNA expression (ON; FIG. 15) and thiamine-containing medium to inhibit antisense RNA production (OFF; FIG. 15). lacZ antisense plasmid pGT2-containing cells grown in the absence of thiamine produced 40% less β-galactosidase than the pREP1 transformants (FIG. 15A). Cells from the same culture grown in the presence of thiamine showed control levels of β-galactosidase activity (FIG. 15B). The reversibility of antisense RNA regulation was demonstrated by transferring cells from thiamine-free medium (ON) to thiamine-containing medium (OFF), and cells from medium containing thiamine (OFF) onto medium lacking thiamine (ON). The pGT2 transformants previously showing 40% reduction in the absence of thiamine exhibited no inhibition of β-galactosidase activity in the presence of thiamine (FIG. 15C). This indicates that repressing lacZ antisense RNA transcription permitted target gene expression to return to the same levels as observed in control pREP1 transformants. In contrast, pGT2 transformants previously exhibiting normal levels of β-galactosidase when grown in the presence of thiamine revealed a 55% decrease in β-galactosidase activity when grown on thiamine-free medium (FIG. 15D). The experiment confirms that the decrease in lacZ gene expression is dependent on transcription of the lacZ antisense gene and the observed reversibility eliminates the involvement of additional genetic effects such as target gene rearrangement.

To further assess the effectiveness of antisense RNA regulation in the present system, partial inhibition of β-galactosidase activity was examined by the long lacZ antisense RNA to determine whether it could modulate the blue colony colour phenotype associated with expression of the lacZ gene in *S. pombe*. Cells containing the lacZ antisense plasmids or the appropriate control vectors were plated on thiamine-free media containing a range of Xgal concentrations. Following extended incubation at 30° C. there was no detectable qualitative difference in the blue colour phenotype exhibited by the long lacZ antisense RNA-expressing cells and those expressing control RNAs. It is concluded that a 55% reduction in β-galactosidase enzyme activity in *S. pombe* is insufficient to alter the visible cellular phenotype.

However, phenotypic readout is still a valuable parameter in the screening process. This was shown in Example 5.

EXAMPLE 7

ANTISENSE SUPPRESSION OF THE lacZ GENE OF *S. POMBE* STRAIN RB3-2 IS DEPENDENT ON THE ANTISENSE RNA LEVEL Strain RB3-2 was transformed with the combinations of plasmids shown in Table 1 with the expected ratios of antisense RNA indicated for each transformation. Three independent transformants for each plasmids combination were assayed in triplicate as hereinbefore described. The data are summariseed in FIG. 16. The data show that for the lacZ target gene, the level of suppression is dependent upon the leve of antisense RNA. For example, the highest level of suppression of approximately 65% is seen when RB3-2 is transformed with the two antisense-encoding plasmids. The plasmids pREP42 and pREP82 encode derivatives of the nmt1 promoter in which mutations have been introduced which result in weaker levels of transcription.

TABLE 1

| Trans-formant | Plasmid 1 | Plasmid 2 | Ratio (Antisense:Target) |
|---|---|---|---|
| 1 | pREP1 | pREP4 | 0:1 |
| 2 | pREP1 | pREP82::antisense | 0.025:1 |
| 3 | pREP1 | pREP42::antisense | 0.3:1 |
| 4 | pREP1 | pREP4::antisense | 2–4:1 |
| 5 | pREP1:antisense | pREP4::antisense | 4–8:1 |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

We claim:

1. A method of identifying a molecule which modulates expression of a target gene or activity of a product of a target gene, said method comprising generating a strain of *Schizosaccharomyces pombe* which expresses said target gene, introducing to said strain of *Schizosaccharomyces pombe* an amount of said molecule to be tested, and determining the effect of said molecule on expression of said target gene or activity of the product of said target gene, wherein the molecule to be tested is an antisense molecule specific to all or part of said target or a ribozyme.

2. A method according to claim 1 wherein the target gene is an exogenous gene of eukaryotic, prokaryotic or viral origin.

3. A method according to claim 1 wherein the target gene is a *S. pombe* homologue of an exogenous gene of eukaryotic, prokaryotic or viral origin.

4. A method according to claim 2 wherein the eukaryotic gene is a mammalian gene.

5. A method according to claim 2 wherein the eukaryotic gene is a plant gene.

6. A method according to claim 2 wherein the viral gene is of HIV or hepatitis virus.

7. A method according to claim 1 wherein the target gene or a portion thereof which is transcribed is fused to a genetic sequence encoding a reporter molecule which provides an identifiable signal. origin.

8. A method according to claim 7 wherein the reporter molecule is an enzyme, a molecule that confers antibiotic resistance, a molecule that confers resistance to a chemical compound, a fluorescent protein, an essential growth factor, a cell cytokine protein or a molecule giving a cell a defined phenotype.

9. A method according to claim 7 wherein the reporter molecule is adenosine phosphoribosyl transferase, neomycin phosphotransferase, β-glucuronidase, chloramphenicol acetyl transferase, firefly luciferase or green fluorescent protein.

10. A method according to claim 1 wherein the target gene is under the control of an endogenous *S. pombe* promoter.

11. A method according to claim 10 wherein the endogenous promoter is the *S. pombe* adh1 promoter.

12. A method according to claim 1 wherein the target gene is under the control of an exogenous promoter.

13. A method according to claim 12 wherein the exogenous promoter is the SV40 promoter.

\* \* \* \* \*